(12) United States Patent
Siegwart et al.

(10) Patent No.: US 12,357,580 B2
(45) Date of Patent: Jul. 15, 2025

(54) LIPID NANOPARTICLE COMPOSITIONS FOR DELIVERY OF MRNA AND LONG NUCLEIC ACIDS

(71) Applicant: The Board of Regents of The University of Texas System, Austin, TX (US)

(72) Inventors: Daniel J. Siegwart, Dallas, TX (US); Qiang Cheng, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 18/744,370

(22) Filed: Jun. 14, 2024

(65) Prior Publication Data

US 2024/0325315 A1 Oct. 3, 2024

Related U.S. Application Data

(63) Continuation-in-part of application No. 18/590,737, filed on Feb. 28, 2024, which is a continuation of application No. 18/534,974, filed on Dec. 11, 2023, now Pat. No. 12,133,924, which is a continuation of application No. 18/529,992, filed on Dec. 5, 2023, now abandoned, which is a continuation of application No. 18/186,105, filed on Mar. 17, 2023, now abandoned, which is a continuation of application No. 17/929,704, filed on Sep. 4, 2022, now Pat. No. 11,648,210, which is a continuation of application No. 17/711,911, filed on Apr. 1, 2022, now Pat. No. 11,510,880, which is a continuation of application No. 17/572,615, filed on Jan. 10, 2022, now Pat. No. 11,590,085, which is a continuation of application No. 17/473,863, filed on Sep. 13, 2021, now Pat. No. 11,304,911, which is a continuation of application No. 17/191,895, filed on Mar. 4, 2021, now Pat. No. 11,229,609, application No. 18/744,370 is a continuation-in-part of application No. 17/124,462, filed on Dec. 16, 2020, now abandoned, said application No. 17/191,895 is a continuation of application No. PCT/US2019/049565, filed on Sep. 4, 2019, said application No. 17/124,462 is a continuation of application No. PCT/US2019/037904, filed on Jun. 19, 2019.

(60) Provisional application No. 62/726,741, filed on Sep. 4, 2018, provisional application No. 62/687,010, filed on Jun. 19, 2018.

(51) Int. Cl.
| | |
|---|---|
| C07H 21/02 | (2006.01) |
| A61K 9/51 | (2006.01) |
| A61K 48/00 | (2006.01) |
| C12N 9/22 | (2006.01) |
| C12N 15/11 | (2006.01) |
| C12N 15/113 | (2010.01) |
| C12N 15/88 | (2006.01) |

(52) U.S. Cl.
CPC ........ *A61K 9/5123* (2013.01); *A61K 48/0033* (2013.01); *C12N 9/22* (2013.01); *C12N 15/11* (2013.01); *C12N 15/111* (2013.01); *C12N 15/113* (2013.01); *C12N 15/88* (2013.01); *C12N 2310/11* (2013.01); *C12N 2310/14* (2013.01); *C12N 2310/20* (2017.05); *C12N 2320/32* (2013.01)

(58) Field of Classification Search
CPC .............................. C12N 15/113; C12N 15/00
See application file for complete search history.

(56) References Cited

U.S. PATENT DOCUMENTS

| | | |
|---|---|---|
| 5,820,873 A | 10/1998 | Choi et al. |
| 7,314,956 B2 | 1/2008 | Li et al. |
| 7,404,969 B2 | 7/2008 | Chen et al. |
| 8,017,804 B2 | 9/2011 | Keil et al. |
| 8,058,069 B2 | 11/2011 | Yaworski et al. |
| 8,450,298 B2 | 5/2013 | Mahon et al. |
| 9,326,939 B2 | 5/2016 | Paulson et al. |
| 9,562,086 B2 | 2/2017 | Upton |
| 11,229,609 B2 | 1/2022 | Cheng et al. |
| 11,247,968 B2 | 2/2022 | Siegwart et al. |
| 11,304,911 B2 | 4/2022 | Cheng et al. |
| 11,510,880 B2 | 11/2022 | Cheng et al. |
| 11,858,884 B2 | 1/2024 | Siegwart et al. |

(Continued)

FOREIGN PATENT DOCUMENTS

| | | |
|---|---|---|
| CN | 101591428 | 5/2011 |
| CN | 103999853 | 8/2014 |

(Continued)

OTHER PUBLICATIONS

Adams et al., "Trial design and rationale for APOLLO, a Phase 3, placebo-controlled study of patisiran in patients with hereditary ATTR amyloidosis with polyneuropathy," *BMC Neurol*, 17(1):181, 2017.

(Continued)

*Primary Examiner* — Amy Rose Hudson
(74) *Attorney, Agent, or Firm* — Parker Highlander PLLC

(57) ABSTRACT

In some aspects, the present disclosure provides compositions of lipid nanoparticles useful for the delivery of large RNAs including mRNAs. These compositions may include a cationic ionizable lipid, a phospholipid, a PEGylated lipid, and a steroid including using less of a cationic ionizable lipid than compositions with shorter nucleic acids. These compositions may be used to treat a disease or disorder for which the delivery of an mRNA is therapeutically effective.

26 Claims, 11 Drawing Sheets
(9 of 11 Drawing Sheet(s) Filed in Color)
Specification includes a Sequence Listing.

(56) References Cited

U.S. PATENT DOCUMENTS

| | | |
|---|---|---|
| 2004/0236015 A1 | 11/2004 | Kozlowski et al. |
| 2005/0008689 A1 | 1/2005 | Semple et al. |
| 2006/0008910 A1 | 1/2006 | MacLachlan et al. |
| 2007/0298006 A1 | 12/2007 | Tomalia et al. |
| 2008/0242626 A1 | 10/2008 | Zugates et al. |
| 2009/0221684 A1 | 9/2009 | Grinstaff et al. |
| 2010/0048888 A1 | 2/2010 | Chen et al. |
| 2010/0178267 A1 | 7/2010 | Puerta et al. |
| 2010/0196277 A1 | 8/2010 | DeSimone et al. |
| 2010/0303884 A1 | 12/2010 | Upton et al. |
| 2011/0009641 A1 | 1/2011 | Anderson et al. |
| 2011/0038941 A1 | 2/2011 | Lee et al. |
| 2011/0165223 A1 | 7/2011 | Sgouros et al. |
| 2013/0171241 A1 | 7/2013 | Geall |
| 2013/0195967 A1 | 8/2013 | Guild et al. |
| 2014/0186332 A1 | 7/2014 | Ezrin et al. |
| 2014/0206753 A1 | 7/2014 | Guild et al. |
| 2014/0371293 A1 | 12/2014 | Brown et al. |
| 2015/0110859 A1 | 4/2015 | Heartlein et al. |
| 2015/0118288 A1 | 4/2015 | Lee |
| 2015/0272886 A1 | 10/2015 | Chen et al. |
| 2015/0297749 A1 | 10/2015 | Hahn et al. |
| 2016/0081944 A1 | 3/2016 | Lee |
| 2016/0158354 A1 | 6/2016 | DeRosa et al. |
| 2016/0220681 A1 | 8/2016 | Siegwart et al. |
| 2016/0317647 A1 | 11/2016 | Ciaramella et al. |
| 2017/0121279 A1 | 5/2017 | Siegwart et al. |
| 2017/0240501 A1 | 8/2017 | DeRosa et al. |
| 2017/0326254 A1 | 11/2017 | Chen et al. |

FOREIGN PATENT DOCUMENTS

| | | |
|---|---|---|
| EP | 3315125 | 5/2018 |
| EP | 3757570 | 12/2020 |
| EP | 3810148 | 4/2021 |
| EP | 3950003 | 2/2022 |
| JP | 2014-103108 | 6/2014 |
| JP | 2014-529328 | 11/2014 |
| JP | 2015-519346 | 7/2015 |
| JP | 2019-515016 | 6/2019 |
| KR | 20110090661 | 8/2011 |
| WO | WO 2006-138380 | 12/2006 |
| WO | WO 2010-053329 | 5/2010 |
| WO | WO 2010-129687 | 11/2010 |
| WO | WO 2010-141069 | 12/2010 |
| WO | WO 2012-090223 | 7/2012 |
| WO | WO 2012-170930 | 12/2012 |
| WO | WO 2012-170952 | 12/2012 |
| WO | WO 2013-177415 | 11/2013 |
| WO | WO 2013-177419 | 11/2013 |
| WO | WO 2014-026283 | 2/2014 |
| WO | WO 2014-105985 | 7/2014 |
| WO | WO 2014-106208 | 7/2014 |
| WO | WO 2014-144196 | 9/2014 |
| WO | WO 2015-089462 | 6/2015 |
| WO | WO 2015-148247 | 10/2015 |
| WO | WO 2015-191693 | 12/2015 |
| WO | WO 2016-010840 | 1/2016 |
| WO | WO 2016-094342 | 6/2016 |
| WO | WO 2016-118697 | 7/2016 |
| WO | WO 2016-118725 | 7/2016 |
| WO | WO 2017-048789 | 3/2017 |
| WO | WO 2017-053713 | 3/2017 |
| WO | WO 2017-173054 | 10/2017 |
| WO | WO 2017-180917 | 10/2017 |
| WO | WO 2017-201091 | 11/2017 |
| WO | WO 2017-201350 | 11/2017 |
| WO | WO 2018-029586 | 2/2018 |
| WO | WO 2018-078053 | 5/2018 |
| WO | WO 2019-246203 | 12/2019 |
| WO | WO 2020-051220 | 3/2020 |
| WO | WO 2020-051223 | 3/2020 |

OTHER PUBLICATIONS

Akinc et al., "A combinatorial library of lipid-like materials for delivery of RNAi therapeutics," *Nat. Biotechnol.*, 26:561-569, 2008.

Amoasii et al., "Gene editing restores dystrophin expression in a canine model of Duchenne muscular dystrophy," *Science*, 362:86-91, 2018.

Bartsch et al., "Massive and selective delivery of lipid-coated cationic lipoplexes of oligonucleotides targeted in vivo to hepatic endothelial cells," *Pharmaceutical Research*, 19(5):676-680, 2002.

Blasco et al., "Simple and rapid in vivo generation of chromosomal rearrangements using CRISPR/Cas9 technology," *Cell Rep.*, 9:1219-1227, 2014.

Bosman et al., "About dendrimers: Structure, physical properties, and applications," *Chem. Rev.*, 99:1665-1688, 1999.

Boyerinas et al., "The role of let-7 in cell differentiation and cancer," *Endocr.-Relat. Cancer*, 17:F19-F36, 2010.

Bryantsev et al., "pKa calculations of aliphatic amines, diamines, and aminoamides via density functional theory with a Poisson-Boltzmann continuum solvent model," *J. Phys. Chem. A.*, 111:4422-4430, 2007.

Carlmark et al., "New methodologies in the construction of dendritic materials," *Chem. Soc. Rev.*, 38:352-362, 2009.

Chatani et al., "Facile and Efficient Synthesis of Dendrimers and One-Pot Preparation of Dendritic-Linear Polymer Conjugates via a Single Chemistry: Utilization of Kinetically Selective Thiol-Michael Addition Reactions," *Macromolecules*, 47:4894-4900, 2014.

Cheng and Lee, "The role of helper lipids in lipid nanoparticles (LNPs) designed for oligonucleotide delivery," *Adv Drug Deliv Rev.*, 99(Pt A):129-137, 2016.

Cheng et al., "Dendrimer-Based Lipid Nanoparticles Deliver Therapeutic FAH mRNA to Normalize Liver Function and Extend Survival in a Mouse Model of Hepatorenal Tyrosinemia Type I," *Adv Mater.*, 30(52):e1805308, 2018.

Cheng et al., "Selective organ targeting (SORT) nanoparticles for tissue-specific mRNA delivery and CRISPR-Cas gene editing," *Nature Nanotechnology*, 15:313-320, 2020.

Chew et al., "A multifunctional AAV-CRISPR-Cas9 and its host response," *Nature methods*, 13:868, 2016.

Coelho et al., "Safety and efficacy of RNAi therapy for transthyretin amyloidosis," *New Engl J Med.*, 369(9):819-829, 2013.

Cong et al., "Multiplex genome engineering using CRISPR/Cas systems," *Science*, 339:819-823, 2013.

Cui et al., "Correlation of the cytotoxic effects of cationic lipids with the headgroups," *Toxicol. Res.*, 7:473, 2018.

Dahlman et al., "In vivo endothelial siRNA delivery using polymeric nanoparticles with low molecular weight," *Nat Nanotechnol*, 9(8):648-655, 2014.

Derosa et al., "Therapeutic efficacy in a hemophilia B model using a biosynthetic mRNA liver depot system," *Gene Ther.*, 23(10):699-707, 2016.

Dong et al., "Lipopeptide nanoparticles for potent and selective siRNA delivery in rodents and nonhuman primates," *Proc. Natl. Acad. Sci. USA*, 111(11):3955-3960, 2014.

Dong et al., "Poly(glycoamidoamine) Brushes Formulated Nanomaterials for Systemic siRNA and mRNA Delivery in Vivo," *Nano Lett.*, 16:842-848, 2016.

Doudna & Charpentier, "Genome editing. The new frontier of genome engineering with CRISPR-Cas9," *Science*, 346:1258096, 2014.

Duncan and Izzo, "Dendrimer biocompatibility and toxicity," *Adv. Drug Deliv. Rev.*, 57:2215-2237, 2005.

Ex parte Rolf Bergmann, Maria Lundqvist, Stig Mannberg, Bjorn Lundgren, and Robert Shimizu, Board of Patent Appeals and Interferences, Appeal 2011-013450, Feb. 1, 2012.

Extended European Search Report issued in European Application No. 16847193.6, mailed Feb. 19, 2019.

Extended European Search Report issued in European Application No. 19857774.4, mailed Jun. 7, 2022.

Extended European Search Report issued in European Application No. 19858575.4, mailed Sep. 12, 2022.

Extended European Search Report issued in European Application No. 19822888.4, mailed May 6, 2022.

(56) References Cited

OTHER PUBLICATIONS

Extended European Search Report issued in European Application No. 17800042.8, mailed Dec. 19, 2019.
Fenton et al., "Bioinspired Alkenyl Amino Alcohol Ionizable Lipid Materials for Highly Potent In Vivo mRNA Delivery," *Adv. Mater.*, 28:2939-2943, 2016.
Fenton et al., "Synthesis and biological evaluation of ionizable lipid materials for the in vivo delivery of messenger RNA to B lymphocytes," *Adv. Mater.*, 29:1606944, 2017.
Finn et al., "A Single Administration of CRISPR/Cas9 Lipid Nanoparticles Achieves Robust and Persistent In Vivo Genome Editing," *Cell Rep.*, 22:2227-2235, 2018.
Franc and Kakkar, "'Click' methodologies: efficient, simple and greener routes to design dendrimers," *Chem. Soc. Rev.*, 39:1536-1544, 2010.
Gilleron et al., "Image-based analysis of lipid nanoparticle-mediated siRNA delivery, intracellular trafficking and endosomal escape," *Nat Biotechnol*, 31(7):638-646, 2013.
Gillies and Fréchet, "Designing macromolecules for therapeutic applications: Polyester dendrimer-poly(ethylene oxide) "bow-tie" hybrids with tunable molecular weight and architecture," *J. Am. Chem. Soc.*, 124:14137-14146, 2002.
Grayson and Fréchet, "Convergent dendrons and dendrimers: From synthesis to applications," *Chem. Rev.*, 101:3819-3868, 2001.
Grompe et al., "Pharmacological correction of neonatal lethal hepatic dysfunction in a murine model of hereditary tyrosinaemia type I," *Nat Genet.*, 10(4):453-460, 1995.
Gustafson et al., "Nanoparticle Uptake: The Phagocyte Problem," *Nano Today*, 10:487-510, 2015.
Hafez et al., "On the mechanism whereby cationic lipids promote intracellular delivery of polynucleic acids," *Gene Ther.*, 8:1188-1196, 2001.
Hajj & Whitehead, "Tools for translation: non-viral materials for therapeutic mRNA delivery," *Nat. Rev. Mater.*, 2:17056, 2017.
Hao et al., "Rapid Synthesis of a Lipocationic Polyester Library via Ring-Opening Polymerization of Functional Valerolactones for Efficacious siRNA Delivery," *Journal of the American Chemical Society*, 137(29):9206-9209, 2015.
Harvie et al., "Characterization of lipid DNA interactions. I. Destabilization of bound lipids and DNA dissociation," *Biophys J.*, 75(2):1040-1051, 1998.
Hendel et al., "Chemically modified guide RNAs enhance CRISPR-Cas genome editing in human primary cells," *Nat. Biotechnol.*, 33:985-989, 2015.
Hoyle et al., "Thiol-click chemistry: a multifaceted toolbox for small molecule and polymer synthesis," *Chem. Soc. Rev.*, 39:1355-1387, 2010.
Jarzbińska et al., "A Single Methylene Group in Oligoalkylamine-Based Cationic Polymers and Lipids Promotes Enhanced mRNA Delivery," *Angew. Chem. Int. Ed.*, 55:9591-9595, 2016.
Jayaraman et al., "Maximizing the potency of siRNA lipid nanoparticles for hepatic gene silencing in vivo," *Angew. Chem. Int. Ed.*, 51:8529-8533, 2012.
Jiang et al., "A non-viral CRISPR/Cas9 delivery system for therapeutically targeting HBV DNA and pcsk9 in vivo," *Cell Research*, 27:440-443, 2017.
Jinek et al., "A programmable dual-RNA-guided DNA endonuclease in adaptive bacterial immunity," *Science*, 337:816-821, 2012.
Kaczmarek et al., "Polymer-Lipid Nanoparticles for Systemic Delivery of mRNA to the Lungs," *Angew. Chem. Int. Ed.*, 55:13808-13812, 2016.
Kanasty et al., "Delivery materials for siRNA therapeutics," *Nat. Mater.*, 12:967-977, 2013.
Kang et al., "Tat-conjugated PAMAM dendrimers as delivery agents for antisense and siRNA oligonucleotides," *Pharm. Res.*, 22:2099-2106, 2005.
Kauffman et al., "Optimization of Lipid Nanoparticle Formulations for mRNA Delivery in Vivo with Fractional Factorial and Definitive Screening Designs," *Nano Lett.*, 15(11):7300-7306, 2015.
Khan et al., "Ionizable amphiphilic dendrimer-based nanomaterials with alkyl-chain-substituted amines for tunable siRNA delivery to the liver endothelium in vivo," *Angew. Chem. Int. Ed.*, 53:14397-14401, 2014.
Killops et al., "Robust, efficient, and orthogonal synthesis of dendrimers via thiol-ene "click" chemistry," *J. Am. Chem. Soc.*, 130:5062-5064, 2008.
Kormann et al., "Expression of therapeutic proteins after delivery of chemically modified mRNA in mice," *Nat. Biotechnol.*, 29:154-157, 2011.
Lee et al., "Designing dendrimers for biological applications," *Nat. Biotechnol.*, 23:1517-1526, 2005.
Leung et al., "Lipid nanoparticles containing siRNA synthesized by microfluidic mixing exhibit an electron-dense nanostructured core," *J. Phys. Chem. C Nanomater Interaces*, 116:18440-18450, 2012.
Li and Szoka, "Lipid-based nanoparticles for nucleic acid delivery," *Pharm Res.*, 24(3):438-449, 2007.
Li et al., "A biomimetic lipid library for gene delivery through thiol-yne click chemistry," *Biomaterials*, 33(32):8160-8166, 2012.
Li et al., "An Orthogonal Array Optimization of Lipid-like Nanoparticles for mRNA Delivery in Vivo," *Nano Lett.*, 15:8099-8107, 2015.
Li et al., "Effects of local structural transformation of lipid-like compounds on delivery of messenger RNA," *Sci. Rep.*, 6:22137, 2016.
Love et al., "Lipid-like materials for low-dose, in vivo gene silencing," *Proc Natl Acad Sci USA*, 107(5):1864-1869, 2010.
Lowe, "mRNA vaccines; what happens," located at https://www.science.org/content/blog-post/mrna-vaccines-what-happens, accessed Jan. 15, 2022, originally published Jan. 21, 2021.
Lowe, "RNA vaccines and their lipids," In the Pipeline, https://blogs.sciencemag.org/pipeline/archives/2021/01/11/rna-vaccines-and-their-lipids, accessed Aug. 19, 2021, originally published Jan. 11, 2021.
Lowe, "What mRNA is good for, and what it maybe isn't," https://www.science.org/content/blog-post/what-mrna-good-and-what-it-maybe-isn-t accessed Jan. 15, 2022, originally published Jun. 29, 2021.
Lu et al., "Toxicity of cationic lipids and cationic polymers in gene delivery," *J. Controlled Release*, 114:100-109, 2006.
Ma et al., "Facile synthesis of polyester dendrimers from sequential click coupling of asymmetrical monomers," *J. Am. Chem. Soc.*, 131(41):14795-14803, 2009.
Maddalo et al., "In vivo engineering of oncogenic chromosomal rearrangements with the CRISPR/Cas9 system," *Nature*, 516:423-427, 2014.
Mali et al., "RNA-guided human genome engineering via Cas9," *Science*, 339:823-826, 2013.
Marshall et al., "Cationic lipid structure and formulation considerations for optimal gene transfection of the lung," *Journal of Drug Targeting*, 7(6):453-469, 2000.
Miller et al., "Non-viral CRISPR/Cas gene editing in vitro and in vivo enabled by synthetic nanoparticle co-delivery of Vas9 mRNA and sgRNA," *Angewandte Chemie*, 56(4):1059-1063, 2016.
Murat and Grest, "Molecular dynamics study of dendrimer molecules in solvents of varying quality," *Macromolecules*, 29:1278-1285, 1996.
Nelson et al., "Balancing cationic and hydrophobic content of PEGylated siRNA polyplexes enhances endosome escape, stability, blood circulation time, and bioactivity in vivo," *ACS Nano*, 7:8870-8880, 2013.
Notice of Allowance issued in U.S. Appl. No. 15/265,064, mailed Oct. 1, 2021.
Notice of Allowance issued in U.S. Appl. No. 17/191,895, mailed Sep. 1, 2021.
Office Action issued in British Application No. 2104769.1, mailed Jun. 1, 2021.
Office Action issued in British Application No. 2104777.4, mailed Jun. 1, 2021.
Office Action issued in British Application No. GB 2219700.8, mailed Feb. 3, 2023.
Office Action issued in British Application No. GB2100678.8, mailed Jun. 11, 2021.

(56) References Cited

OTHER PUBLICATIONS

Office Action issued in British Application No. GB2104777.4, mailed Mar. 2, 2022.
Office Action issued in British Application No. GB2111272.7, mailed Mar. 2, 2022.
Office Action issued in Chinese Application No. 201980070622.2, mailed Nov. 28, 2023, and English translation thereof.
Office Action issued in Japanese Application No. 2018-513463, mailed Sep. 7, 2020.
Office Action issued in Japanese Application No. 2021-536681, mailed Nov. 9, 2022.
Office Action issued in U.S. Appl. No. 15/265,064, mailed Aug. 3, 2020.
Office Action issued in U.S. Appl. No. 15/597,063, mailed Apr. 22, 2020.
Office Action issued in U.S. Appl. No. 15/597,063, mailed Aug. 22, 2019.
Office Action issued in U.S. Appl. No. 17/124,462, mailed Apr. 22, 2021.
Office Action issued in U.S. Appl. No. 17/124,462, mailed Apr. 6, 2023.
Office Action issued in U.S. Appl. No. 17/124,462, mailed Jul. 12, 2021.
Office Action issued in U.S. Appl. No. 17/124,462, mailed Jun. 22, 2022.
Office Action issued in U.S. Appl. No. 17/124,462, mailed Jan. 25, 2024.
Office Action issued in U.S. Appl. No. 17/124,462, mailed Nov. 15, 2021.
Office Action issued in U.S. Appl. No. 17/124,462, mailed Sep. 20, 2022.
Office Action issued in U.S. Appl. No. 17/191,895, mailed Jun. 16, 2021.
Office Action issued in U.S. Appl. No. 17/191,975, mailed Aug. 25, 2021.
Office Action issued in U.S. Appl. No. 17/191,975, mailed Dec. 14, 2022.
Office Action issued in U.S. Appl. No. 17/191,975, mailed Feb. 11, 2022.
Office Action issued in U.S. Appl. No. 17/191,975, mailed Jul. 26, 2022.
Office Action issued in U.S. Appl. No. 17/191,975, mailed Nov. 1, 2021.
Office Action issued in U.S. Appl. No. 17/572,615, mailed Mar. 24, 2022.
Office Action issued in U.S. Appl. No. 17/572,615, mailed May 5, 2022.
Office Action issued in U.S. Appl. No. 17/839,699, mailed Sep. 6, 2022.
Office Action issued in U.S. Appl. No. 17/929,704, mailed Oct. 28, 2022.
Office Action issued in U.S. Appl. No. 18/534,974, mailed Feb. 16, 2024.
Pankowicz et al., "Reprogramming metabolic pathways in vivo with CRISPR/Cas9 genome editing to treat hereditary tyrosinaemia," *Nat Commun.*, 7:12642, 2016.
Pardi et al., "Expression kinetics of nucleoside-modified mRNA delivered in lipid nanoparticles to mice by various routes," *J.Controlled Release*, 217:345-351, 2015.
Patel et al., "Boosting Intracellular Delivery of Lipid Nanoparticle-Encapsulated mRNA," *Nano Lett*, 17:5711-5718, 2017.
PCT International Preliminary Report on Patentability issued in International Application No. PCT/US2019/049552, mailed Mar. 18, 2021.
PCT International Preliminary Report on Patentability issued in International Application No. PCT/US2019/049565, mailed Mar. 18, 2021.
PCT International Search Report and Written Opinion issued in International Application No. PCT/US2019/037904, mailed Oct. 2, 2019.
PCT International Search Report and Written Opinion issued in International Application No. PCT/US2016/051648, mailed Feb. 7, 2017.
PCT International Search Report and Written Opinion issued in International Application No. PCT/US2019/049552, mailed Dec. 30, 2019.
PCT International Search Report and Written Opinion issued in International Application No. PCT/US2019/049565, mailed Feb. 7, 2020.
PCT International Search Report and Written Opinion issued in International Application No. PCT/US2017/032967, mailed Aug. 11, 2017.
Percec et al., "Self-assembly of Janus dendrimers into uniform dendrimersomes and other complex architectures," *Science*, 328:1009-1014, 2010.
Petsch et al., "Protective efficacy of in vitro synthesized, specific mRNA vaccines against influenza A virus infection," *Nat. Biotechnol*, 30:1210-1216, 2012.
Ramaswamy et al., "Systemic delivery of factor IX messenger RNA for protein replacement therapy," *Proc. Natl. Acad. Sci. U.S.A.*, 114:E1941-E1950, 2017.
Regnaud, "Design and synthesis of dendrimers by combination of 'click' chemistry and A3-coupling," Thesis, McGill University, pp. 1-67, 2013.
Richner et al., "Modified mRNA Vaccines Protect against Zika Virus Infection," *Cell*, 169:176, 2017.
Sahay et al., "Efficiency of siRNA delivery by lipid nanoparticles is limited by endocytic recycling," *Nat. Biotechnol.*, 31(7):653-658, 2013.
Sahin et al., "mRNA-based therapeutics—developing a new class of drugs," *Nat. Rev. Drug Discovery*, 13:759-780, 2014.
Sander & Joung, "CRISPR-Cas systems for editing, regulating and targeting genomes," Nat. Biotechnol., 32:347-355, 2014.
Schaffert et al., "Solid-phase synthesis of sequence-defined T-, i-, and U-shape polymers for pDNA and siRNA delivery," *Angew. Chem. Int. Ed.*, 50:8986-8989, 2011.
Semple et al., "Rational design of cationic lipids for siRNA delivery," *Nat. Biotechnol.*, 28:172-176, 2010.
Shobaki et al., "Mixing lipids to manipulate the ionization status of lipid nanoparticles for specific tissue targeting," *International Journal of Nanomedicine*, 13:8395-8410, 2018.
Siegwart et al., "Combinatorial synthesis of chemically diverse core-shell nanoparticles for intracellular delivery," *Proc. Natl. Acad. Sci. U.S.A.*, 108:12996-13001, 2011.
Staahl et al., "Efficient genome editing in the mouse brain by local delivery of engineered Cas9 ribonucleoprotein complexes," *Nat. Biotechnol.*, 35:431-434, 2017.
Stiriba et al., "Dendritic polymers in biomedical applications: From potential to clinical use in diagnostics and therapy," *Angew. Chem. Int. Ed.*, 41:1329-1334, 2002.
Sun et al., "Self-assembled DNA nanoclews for the efficient delivery of CRISPR-Cas9 for genome editing," *Angew. Chem. Int. Ed.*, 54:12029-12033, 2015.
Sundaram et al., "Reversibly switchable polymer with cationic/zwitterionic/anionic behavior through synergistic protonation and deprotonation," *Chem. Sci.*, 5:200-205, 2014.
Tabebordbar et al., "In vivo gene editing in dystrophic mouse muscle and muscle stem cells," Science, 351:407-411, 2016.
Taratula et al., "Surface-engineered targeted PPI dendrimer for efficient intracellular and intratumoral siRNA delivery," *J. Control. Release*, 140:284-293, 2009.
Tousignant et al., "Comprehensive analysis of the acute toxicity systemic administration of cationic lipid:plasmid DNA complexes in mice," *Hum. Gene Ther.*, 11:2493-2513, 2000.
Uchida et al., "Modulated protonation of side chain aminoethylene repeats in N-substituted polyaspartamides promotes mRNA transfection," *J. Am. Chem. Soc.*, 136:12396-12405, 2014.
Wang et al., "Cas9-mediated allelic exchange repairs compound heterozygous recessive mutations in mice," Nat. Biotechnol., 36(9):839-842, 2018.
Wang et al., "CRISPR/Cas9-Based Genome Editing for Disease Modeling and Therapy: Challenges and Opportunities for Nonviral Delivery," *Chem. Rev.*, 117:9874-9906, 2017.

(56) References Cited

OTHER PUBLICATIONS

Whitehead et al., "Degradable lipid nanoparticles with predictable in vivo siRNA delivery activity," *Nat. Commun.*, 5:4277, 2014.
Wilhelm et al., "Analysis of nanoparticle delivery to tumours," *Nat. Rev. Mater.*, 1:16014, 2016.
Wittrup et al., "Visualizing lipid-formulated siRNA release from endosomes and target gene knockdown," *Nat Biotechnol.*, 33:870-876, 2015.
Wood, "Traumatic brain injury induces transmissible tau pathology," *Nat. Rev. Neurol.*, 14:570-571, 2018.
Wu et al., "Dendrimers in medicine: Therapeutic concepts and pharmaceutical challenges," *Bioconjugate Chem.*, 26(7):1198-1211, 2015.
Wu et al., "Efficiency and fidelity in a click-chemistry route to triazole dendrimers by the copper(I)-catalyzed ligation of azides and alkynes," *Angew. Chem. Int. Ed.*, 43:3928-3932, 2004.
Wu et al., "RNAi therapies: drugging the undruggable," *Sci. Transl. Med.*, 6:240-247, 2014.
Xu et al., "Fluorescent water-soluble perylenediimide-cored cationic dendrimers: synthesis, optical properties, and cell uptake," *Chem. Commun.*, 49:3646-3648, 2013.
Xue et al., "CRISPR-mediated direct mutation of cancer genes in the mouse liver," Nature, 514:380-384, 2014.
Yan et al., "Functional polyesters enable selective siRNA delivery to lung cancer over matched normal cells," *Proc. Natl. Acad. Sci.*, 113:E5702-E5710, 2016.
Yan et al., "Systemic mRNA Delivery to the Lungs by Functional Polyester-based Carriers," *Biomacromolecules*, 18:4307-4315, 2017.
Yin et al., "Genome editing with Cas9 in adult mice corrects a disease mutation and phenotype," *Nat Biotechnol.*, 32:551-553, 2014.
Yin et al., "Structure-guided chemical modification of guide RNA enables potent non-viral in vivo genome editing," Nat. Biotechnol., 35:1179-1187, 2017.
Yin et al., "Therapeutic genome editing by combined viral and non-viral delivery of CRISPR system components in vivo," *Nat. Biotechnol.*, 34:328-333, 2016.
Yu et al., "An amphiphilic dendrimer for effective delivery of small interfering RNA and gene silencing in vitro and in vivo," *Angewandte Chem. Int. Ed.*, 51:8478-8484, 2012.
Yung et al., "Lipid nanoparticles composed of quaternary amine-tertiary amine cationic lipid combination (QTsome) for therapeutic delivery of antimiR-21 for lung cancer," *Molecular Pharmaceutics*, 13:653-662, 2016.
Zelphati and Szoca, "Intracellular distribution and mechanism of delivery of oligonucleotides mediated by cationic lipids," *Pharm Res.*, 13:1367-1372, 1996.
Zhang et al., "Biodegradable amino-ester nanomaterials for Cas9 mRNA delivery in vitro and in vivo," *ACS Appl Mater Interfaces*, 9(30):25481-25487, 2017.
Zhang et al., "Knockdown of Anillin Actin Binding Protein Blocks Cytokinesis in Hepatocytes and Reduces Liver Tumor Development in Mice Without Affecting Regeneration," *Gastroenterology*, 154(5):1421-1434, 2018.
Zhang et al., "The Polyploid State Plays a Tumor-Suppressive Role in the Liver," *Dev. Cell*, 44(4):447-459, 2018.
Zhou et al., "Balancing biocompatibility, internalization and pharmacokinetics of polycations/siRNA by structuring the weak negative charged ternary complexes with hyaluronic acid," *Journal of Biomedical Nanotechnology*, 13:1533-1544, 2017.
Zhou et al., "Modular degradable dendrimers enable small RNAs to extend survival in an aggressive liver cancer model," *Proc. Natl. Acad. Sci. USA*, 113(3):520-525, 2016.
Zhou et al., "Modular degradable dendrimers enable small RNAs to extend survival in an aggressive liver cancer model," Supporting Information, *Proc. Natl. Acad. Sci. USA*, 2016.
Zhou et al., "PAMAM dendrimers for efficient siRNA delivery and potent gene silencing," *Chem. Commun.*, 22:2362-2364, 2006.
Zuris et al., "Cationic lipid-mediated delivery of proteins enables efficient protein-based genome editing in vitro and in vivo," Nat. Biotechnol., 33:73-80, 2015.

| Library A | | | | | | | | |
|---|---|---|---|---|---|---|---|---|
| Name | Molar Ratios | | | | Molar Percentage (%) | | | | 5A2-SC8/ mRNA (wt/wt) |
| | 5A2-SC8 | DOPE | Chol | DMG-PEG | 5A2-SC8 | DOPE | Chol | DMG-PEG | |
| A1 | 15 | 10 | 20 | 0.5 | 32.97 | 21.98 | 43.96 | 1.10 | 20 |
| A2 | 15 | 20 | 25 | 1 | 24.59 | 32.79 | 40.98 | 1.64 | 20 |
| A3 | 15 | 30 | 30 | 2.5 | 19.35 | 38.71 | 38.71 | 3.23 | 20 |
| A4 | 15 | 40 | 35 | 5 | 15.79 | 42.11 | 36.84 | 5.26 | 20 |
| A5 | 25 | 10 | 25 | 2.5 | 40.00 | 16.00 | 40.00 | 4.00 | 20 |
| A6 | 25 | 20 | 20 | 5 | 35.71 | 28.57 | 28.57 | 7.14 | 20 |
| A7 | 25 | 30 | 35 | 0.5 | 27.62 | 33.15 | 38.67 | 0.55 | 20 |
| A8 | 25 | 40 | 30 | 1 | 26.04 | 41.67 | 31.25 | 1.04 | 20 |
| A9 | 35 | 10 | 30 | 5 | 43.75 | 12.50 | 37.50 | 6.25 | 20 |
| A10 | 35 | 20 | 35 | 2.5 | 37.84 | 21.62 | 37.84 | 2.70 | 20 |
| A11 | 35 | 30 | 20 | 1 | 40.70 | 34.88 | 23.26 | 1.16 | 20 |
| A12 | 35 | 40 | 25 | 0.5 | 34.83 | 39.80 | 24.88 | 0.50 | 20 |
| A13 | 45 | 10 | 35 | 1 | 49.45 | 10.99 | 38.46 | 1.10 | 20 |
| A14 | 45 | 20 | 30 | 0.5 | 47.12 | 20.94 | 31.41 | 0.52 | 20 |
| A15 | 45 | 30 | 25 | 5 | 42.86 | 28.57 | 23.81 | 4.76 | 20 |
| A16 | 45 | 40 | 20 | 2.5 | 41.86 | 37.21 | 18.60 | 2.33 | 20 |

| Library B | | | | | | | | |
|---|---|---|---|---|---|---|---|---|
| Name | Molar Ratios | | | | Molar Percentage (%) | | | | 5A2-SC8/ mRNA (wt/wt) |
| | 5A2-SC8 | DOPE | Chol | DMG-PEG | 5A2-SC8 | DOPE | Chol | DMG-PEG | |
| B1 | 5 | 10 | 15 | 0 | 16.67 | 33.33 | 50.00 | 0.00 | 20 |
| B2 | 5 | 15 | 20 | 0.5 | 12.35 | 37.04 | 49.38 | 1.23 | 20 |
| B3 | 5 | 20 | 25 | 1 | 9.80 | 39.22 | 49.02 | 1.96 | 20 |
| B4 | 5 | 25 | 30 | 2 | 8.06 | 40.32 | 48.39 | 3.23 | 20 |
| B5 | 10 | 10 | 20 | 1 | 24.39 | 24.39 | 48.78 | 2.44 | 20 |
| B6 | 10 | 15 | 15 | 2 | 23.81 | 35.71 | 35.71 | 4.76 | 20 |
| B7 | 10 | 20 | 30 | 0 | 16.67 | 33.33 | 50.00 | 0.00 | 20 |
| B8 | 10 | 25 | 25 | 0.5 | 16.53 | 41.32 | 41.32 | 0.83 | 20 |
| B9 | 15 | 10 | 25 | 2 | 28.85 | 19.23 | 48.08 | 3.85 | 20 |
| B10 | 15 | 15 | 30 | 1 | 24.59 | 24.59 | 49.18 | 1.64 | 20 |
| B11 | 15 | 20 | 15 | 0.5 | 29.70 | 39.60 | 29.70 | 0.99 | 20 |
| B12 | 15 | 25 | 20 | 0 | 25.00 | 41.67 | 33.33 | 0.00 | 20 |
| B13 | 20 | 10 | 30 | 0.5 | 33.06 | 16.53 | 49.59 | 0.83 | 20 |
| B14 | 20 | 15 | 25 | 0 | 33.33 | 25.00 | 41.67 | 0.00 | 20 |
| B15 | 20 | 20 | 20 | 2 | 32.26 | 32.26 | 32.26 | 3.23 | 20 |
| B16 | 20 | 25 | 15 | 1 | 32.79 | 40.98 | 24.59 | 1.64 | 20 |

FIG. 2A

| Name | Size (nm) | PDI | Zeta Potential (mV) | Name | Size (nm) | PDI | Zeta Potential (mV) | Name | Size (nm) | PDI | Zeta Potential (mV) |
|---|---|---|---|---|---|---|---|---|---|---|---|
| A1 | 80.48 | 0.11 | 0.46 | B1 | 655.43 | 0.24 | -7.05 | C1 | 73.13 | 0.21 | -0.44 |
| A2 | 95.60 | 0.28 | -4.81 | B2 | 86.31 | 0.16 | -0.08 | C2 | 90.19 | 0.25 | 0.51 |
| A3 | 84.23 | 0.28 | -0.76 | B3 | 73.85 | 0.22 | -2.49 | C3 | 92.18 | 0.20 | -0.90 |
| A4 | 87.46 | 0.39 | 1.55 | B4 | 90.90 | 0.31 | -0.11 | C4 | 100.36 | 0.33 | -0.78 |
| A5 | 87.10 | 0.26 | -0.31 | B5 | 80.65 | 0.26 | -0.19 | C5 | 81.76 | 0.27 | -2.03 |
| A6 | 69.88 | 0.23 | -2.50 | B6 | 98.19 | 0.38 | -0.31 | C6 | 69.83 | 0.13 | -0.87 |
| A7 | 113.93 | 0.15 | -0.73 | B7 | 670.13 | 0.16 | -8.47 | C7 | 94.91 | 0.23 | -1.01 |
| A8 | 91.34 | 0.18 | -1.69 | B8 | 93.62 | 0.20 | 0.17 | C8 | 79.43 | 0.19 | -1.45 |
| A9 | 87.13 | 0.14 | -0.42 | B9 | 94.12 | 0.36 | -1.01 | C9 | 74.63 | 0.24 | -0.52 |
| A10 | 86.60 | 0.15 | -1.31 | B10 | 79.91 | 0.17 | -2.35 | C10 | 99.01 | 0.23 | -3.60 |
| A11 | 113.83 | 0.19 | -2.81 | B11 | 89.66 | 0.19 | -3.03 | C11 | 81.37 | 0.23 | -2.03 |
| A12 | 120.70 | 0.20 | -2.03 | B12 | 837.93 | 0.20 | -7.77 | C12 | 99.19 | 0.24 | -1.85 |
| A13 | 120.97 | 0.17 | -2.79 | B13 | 99.93 | 0.13 | -0.59 | | | | |
| A14 | 135.10 | 0.12 | -4.82 | B14 | 654.57 | 0.19 | -12.27 | | | | |
| A15 | 89.99 | 0.28 | -2.57 | B15 | 69.79 | 0.25 | -2.27 | | | | |
| A16 | 117.07 | 0.17 | -2.32 | B16 | 77.42 | 0.19 | -4.98 | | | | |

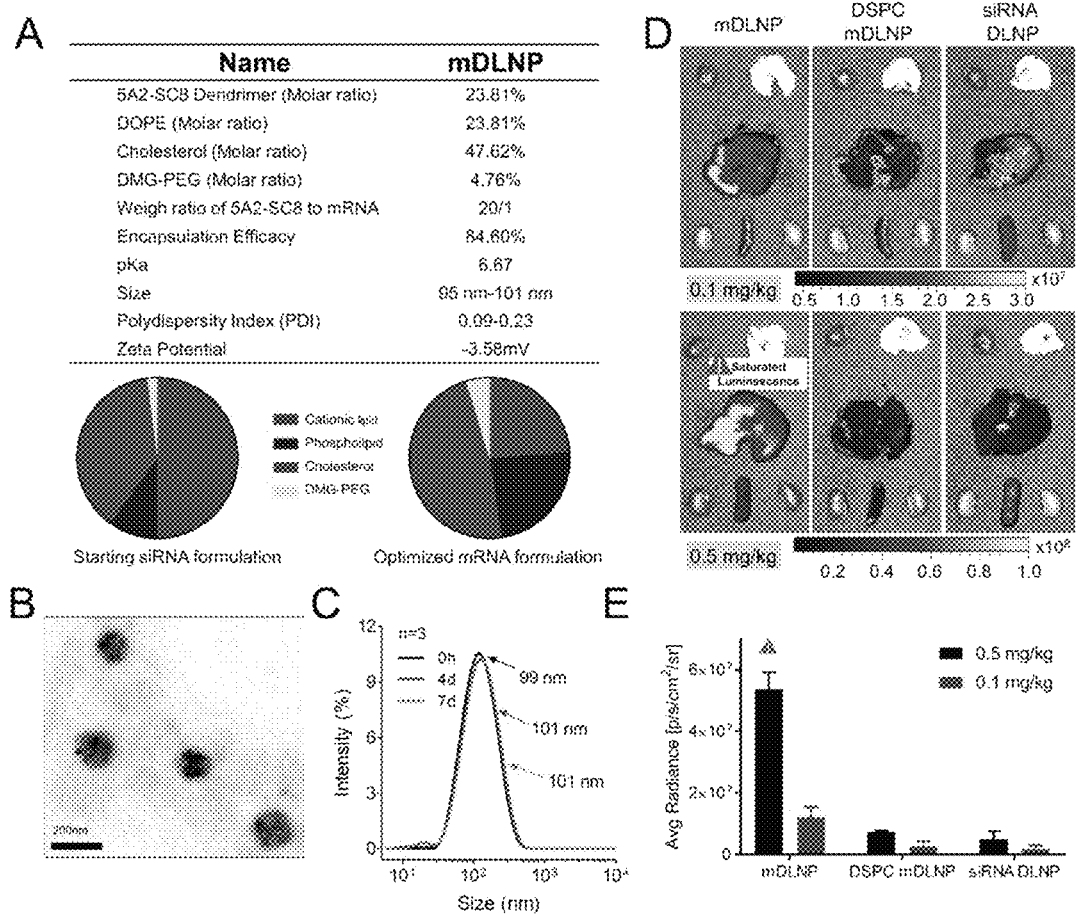
FIGS. 6A-E

LIPID NANOPARTICLE COMPOSITIONS FOR DELIVERY OF MRNA AND LONG NUCLEIC ACIDS

This application is a continuation-in-part of U.S. application Ser. No. 17/124,462, filed Dec. 16, 2020, which is continuation of International Application No. PCT/US2019/037904, filed Jun. 19, 2019, which claims the benefit of priority to U.S. Provisional Application No. 62/687,010, filed Jun. 19, 2018. This application is also a continuation-in-part of U.S. application Ser. No. 18/590,737, filed Feb. 28, 2024, which is a continuation of U.S. application Ser. No. 18/534,974, filed Dec. 11, 2023, which is a continuation of U.S. application Ser. No. 18/529,992, filed Dec. 5, 2023, which is a continuation of U.S. application Ser. No. 18/186,105, filed Mar. 17, 2023, now abandoned, which is a continuation of U.S. application Ser. No. 17/929,704, filed Sep. 4, 2022, now U.S. Pat. No. 11,648,210, which is a continuation of U.S. application Ser. No. 17/711,911, filed Apr. 1, 2022, now U.S. Pat. No. 11,510,880, which is a continuation of U.S. application Ser. No. 17/572,615, filed Jan. 10, 2022, now U.S. Pat. No. 11,590,085, which is a continuation of U.S. application Ser. No. 17/473,863, filed Sep. 13, 2021, now U.S. Pat. No. 11,304,911, which is a continuation of U.S. application Ser. No. 17/191,895, filed Mar. 4, 2021, now U.S. Pat. No. 11,229,609, which is a continuation of International Application No. PCT/US2019/049565, filed Sep. 4, 2019, which claims the benefit of priority to U.S. Provisional Application Ser. No. 62/726,741, filed on Sep. 4, 2018, the entire contents of each of which are hereby incorporated by reference.

This invention was made with government support under Grant No. CA 150245P3 awarded by the Department of Defense. The government has certain rights in the invention.

This application contains a Sequence Listing XML, which has been submitted electronically and is hereby incorporated by reference in its entirety. Said XML Sequence Listing, created on Jun. 13, 2024, is named UTSDP3366USCP1.xml and is 5,371 bytes in size.

BACKGROUND OF THE INVENTION

1. Field of the Invention

The present invention relates generally to the fields of nucleic acid delivery compositions. In particular, it relates to lipid nucleic acid delivery compositions formulated for delivery of larger nucleic acids such as mRNAs. More particularly, it relates to compositions for delivery of mRNAs for the treatment of diseases or disorders.

2. Description of Related Art

Lipid nanoparticles (LNPs) have been widely employed to deliver short RNAs (siRNA/miRNA) to the liver, including in human clinical trials (Kanasty et al., 2013, Coelho et al., 2013 and Adams et al., 2017), but it remains challenging to rationally redesign LNPs for delivery of much longer cargo such as mRNA (Sahin et al., 2014, Hajj & Whitehead, 2017, Kormann et al., 2011; Petsch et al., 2012; Uchida et al., 2014; Kauffman et al., 2015; Li et al., 2015, Pardi et al., 2015, Fenton et al., 2016, Jarzebinska et al., 2016, Kaczmarek et al., 2016, DeRosa et al., 2016, Ramaswamy et al., 2017, Richner et al., 2017 and Patel et al., 2017), particularly for applications in severe disease models, where it is known that lipids can exasperate the underlying disease and abate efficacy (Wu et al., 2014, Tousignant et al., 2000 and Lv et al., 2006). Efficacious carriers would have to be highly tolerated in patients with compromised liver function, as well as be fundamentally altered in their molar composition to accommodate high loading of long mRNAs with potential for secondary folding and increased electrostatic binding. Therefore, there remains a need to identify and develop compositions which can be used to delivery longer mRNAs.

SUMMARY OF THE INVENTION

In some aspects, the present disclosure provides compositions useful for the delivery of long nucleic acids such as mRNAs. In some embodiments, the compositions comprises:
(A) a nucleic acid, wherein the length is greater than 80 nucleotides; and
(B) a delivery lipid nanoparticle composition:
  (i) from about 5 to about 50 of a cationic ionizable lipid;
  (ii) from about 10 to about 45 of a phospholipid;
  (iii) from about 15 to about 50 of a steroid; and
  (iv) from about 0.5 to about 10 of a PEGylated lipid;
  wherein the amounts are as a molar ratio.

In some embodiments, the length of the nucleic acid is from about 90 nucleotides to about 500 nucleotides. In other embodiments, the length of the nucleic acid is from about 1,000 nucleotides to about 7,000 nucleotides. In some embodiments, the nucleic acid is a messenger RNA (mRNA) or a single guide RNA (sgRNA). In some embodiments, the nucleic acid encodes for a protein or a guide for gene editing. In some embodiments, the nucleic acid encodes for or acts in gene editing of a protein that is defective in a disease or disorder.

In some embodiments, the cationic ionizable lipid is a cationic ionizable dendron or a cationic ionizable dendrimer. In some embodiments, the cationic ionizable lipid contains two or more hydrophobic groups, a group which is cationic at physiological pH, a linker group which contains one or more esters. In some embodiments, the cationic ionizable lipid is further defined as a dendron of the formula:
Core-Repeating Unit-Terminating Group (I)
  wherein the core is linked to the repeating unit by removing one or more hydrogen atoms from the core and replacing the atom with the repeating unit and wherein:
  the core has the formula:

wherein:
  $X_1$ is amino or alkylamino$_{(C \leq 12)}$, dialkylamino$_{(C \leq 12)}$, heterocycloalkyl$_{(C \leq 12)}$, heteroaryl$_{(C \leq 12)}$, or a substituted version thereof;
  $R_1$ is amino, hydroxy, or mercapto, or alkylamino$_{(C \leq 12)}$, dialkylamino$_{(C \leq 12)}$, or a substituted version of either of these groups; and
  a is 1, 2, 3, 4, 5, or 6; or
the core has the formula:

wherein:
- $X_2$ is $N(R_5)_y$;
- $R_5$ is hydrogen, alkyl$_{(C\leq18)}$, or substituted alkyl$_{(C\leq18)}$; and
- y is 0, 1, or 2, provided that the sum of y and z is 3;
- $R_2$ is amino, hydroxy, or mercapto, or alkylamino$_{(C\leq12)}$, dialkylamino$_{(C\leq12)}$, or a substituted version of either of these groups;
- b is 1, 2, 3, 4, 5, or 6; and
- z is 1, 2, 3; provided that the sum of z and y is 3; or the core has the formula:

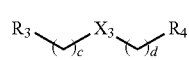

(IV)

wherein:
- $X_3$ is —NR$_6$—, wherein $R_6$ is hydrogen, alkyl$_{(C\leq8)}$, or substituted alkyl$_{(C\leq8)}$, —O—, or alkylaminodiyl$_{(C\leq8)}$, alkoxydiyl$_{(C\leq8)}$, arenediyl$_{(C\leq8)}$, heteroarenediyl$_{(C\leq8)}$, heterocycloalkanediyl$_{(C\leq8)}$, or a substituted version of any of these groups;
- $R_3$ and $R_4$ are each independently amino, hydroxy, or mercapto, or alkylamino$_{(C\leq12)}$, dialkylamino$_{(C\leq12)}$, or a substituted version of either of these groups; or a group of the formula: —N(R$_f$)(CH$_2$CH$_2$N)$_e$(R$_c$)R$_d$;
  - wherein:
    - e and f are each independently 1, 2, or 3; provided that the sum of e and f is 3;
    - $R_c$, $R_d$, and $R_f$ are each independently hydrogen, alkyl$_{(C\leq6)}$, or substituted alkyl$_{(C\leq6)}$;
- c and d are each independently 1, 2, 3, 4, 5, or 6; or
- the core is alkylamine$_{(C\leq18)}$, dialkylamine$_{(C\leq36)}$, heterocycloalkane$_{(C\leq12)}$, or a substituted version of any of these groups;

wherein the repeating unit comprises a degradable diacyl and a linker;
the degradable diacyl group has the formula:

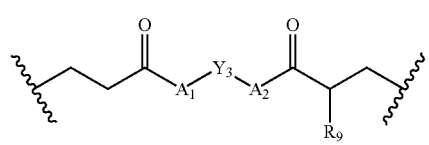

(VII)

wherein:
- $A_1$ and $A_2$ are each independently —O— or —NR$_a$—, wherein:
  - $R_a$ is hydrogen, alkyl$_{(C\leq6)}$, or substituted alkyl$_{(C\leq6)}$;
- $Y_3$ is alkanediyl$_{(C\leq12)}$, alkenediyl$_{(C\leq12)}$, arenediyl$_{(C\leq12)}$, or a substituted version of any of these groups; or a group of the formula:

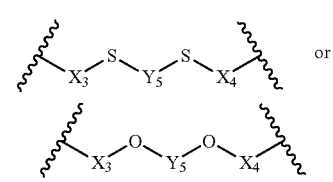

or wherein:
- $X_3$ and $X_4$ are alkanediyl$_{(C\leq12)}$, alkenediyl$_{(C\leq12)}$, arenediyl$_{(C\leq12)}$, or a substituted version of any of these groups;
- $Y_5$ is a covalent bond, alkanediyl$_{(C\leq12)}$, alkenediyl$_{(C\leq12)}$, arenediyl$_{(C\leq12)}$, or a substituted version of any of these groups; and
- $R_9$ is alkyl$_{(C\leq8)}$ or substituted alkyl$_{(C\leq8)}$;

the linker group has the formula:

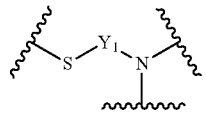

(VI)

wherein:
- $Y_1$ is alkanediyl$_{(C\leq12)}$, alkenediyl$_{(C\leq12)}$, arenediyl$_{(C\leq12)}$, or a substituted version of any of these groups; and wherein when the repeating unit comprises a linker group, then the linker group comprises an independent degradable diacyl group attached to both the nitrogen and the sulfur atoms of the linker group if n is greater than 1, wherein the first group in the repeating unit is a degradable diacyl group, wherein for each linker group, the next repeating unit comprises two degradable diacyl groups attached to the nitrogen atom of the linker group; and wherein n is the number of linker groups present in the repeating unit; and the terminating group has the formula:

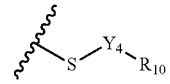

(VIII)

wherein:
- $Y_4$ is alkanediyl$_{(C\leq18)}$ or an alkanediyl$_{(C\leq18)}$ wherein one or more of the hydrogen atoms on the alkanediyl$_{(C\leq18)}$ has been replaced with —OH, —F, —Cl, —Br, —I, —SH, —OCH$_3$, —OCH$_2$CH$_3$, —SCH$_3$, or —OC(O)CH$_3$;
- $R_{10}$ is hydrogen, carboxy, hydroxy, or aryl$_{(C\leq12)}$, alkylamino$_{(C\leq12)}$, dialkylamino$_{(C\leq12)}$, N-heterocycloalkyl$_{(C\leq12)}$, —C(O)N(R$_{11}$)-alkanediyl$_{(C\leq6)}$-heterocycloalkyl$_{(C\leq12)}$, —C(O)-alkyl-amino$_{(C\leq12)}$, —C(O)-dialkylamino$_{(C\leq12)}$, —C(O)—N-heterocyclo-alkyl$_{(C\leq12)}$, wherein:
  - $R_{11}$ is hydrogen, alkyl$_{(C\leq6)}$, or substituted alkyl$_{(C\leq6)}$;
- wherein the final degradable diacyl in the chain is attached to a terminating group;
- n is 0, 1, 2, 3, 4, 5, or 6;

or a pharmaceutically acceptable salt thereof.

In some embodiments, the terminating group is further defined by the formula:

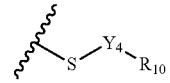

(VIII)

wherein:
Y₄ is alkanediyl$_{(C≤18)}$; and
R₁₀ is hydrogen.

In some embodiments, the core is further defined by the formula:

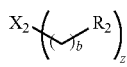
(III)

wherein:
X₂ is N (R₅)$_y$;
R₅ is hydrogen or alkyl$_{(C≤8)}$, or substituted alkyl$_{(C≤18)}$; and
y is 0, 1, or 2, provided that the sum of y and z is 3;
R₂ is amino, hydroxy, or mercapto, or alkylamino$_{(C≤12)}$, dialkylamino$_{(C≤12)}$, or a substituted version of either of these groups;
b is 1, 2, 3, 4, 5, or 6; and
z is 1, 2, 3; provided that the sum of z and y is 3.

In some embodiments, the core is further defined by the formula:

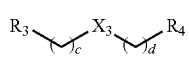
(IV)

wherein:
X₃ is —NR₆—, wherein R₆ is hydrogen, alkyl$_{(C≤8)}$, or substituted alkyl$_{(C≤8)}$, —O—, or alkylaminodiyl$_{(C≤8)}$, alkoxydiyl$_{(C≤8)}$, arenediyl$_{(C≤8)}$, heteroarenediyl$_{(C≤8)}$, heterocycloalkanediyl$_{(C≤8)}$, or a substituted version of any of these groups;
R₃ and R₄ are each independently amino, hydroxy, or mercapto, or alkylamino$_{(C≤12)}$, dialkylamino$_{(C≤12)}$, or a substituted version of either of these groups; or a group of the formula: —N(R$_f$)$_f$(CH₂CH₂N)$_e$(R$_c$)R$_d$;
wherein:
e and f are each independently 1, 2, or 3; provided that the sum of e and f is 3;
R$_c$, R$_d$, and R$_f$ are each independently hydrogen, alkyl$_{(C≤6)}$, or substituted alkyl$_{(C≤6)}$;
c and d are each independently 1, 2, 3, 4, 5, or 6.

In some embodiments, the core is further defined as:

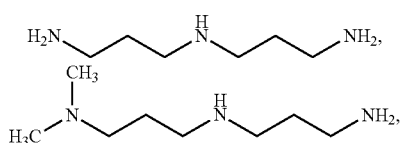

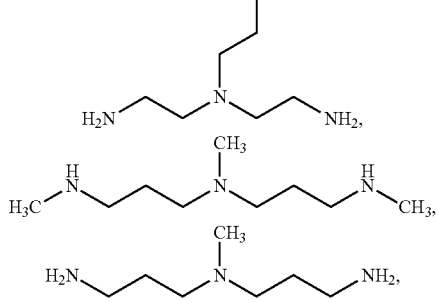

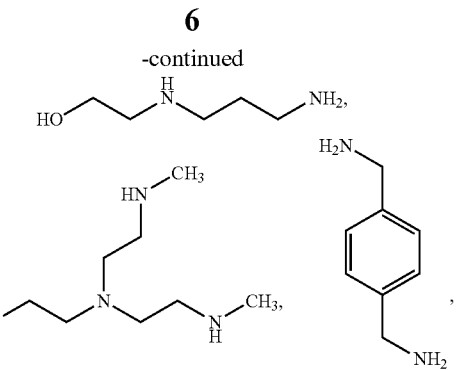

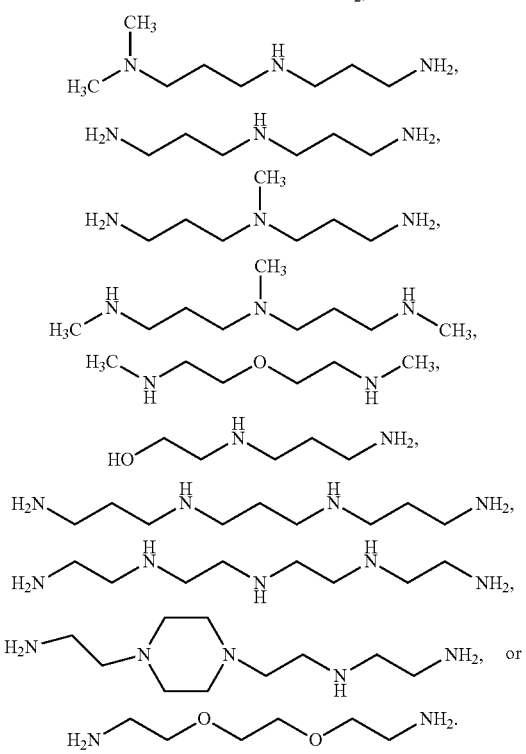

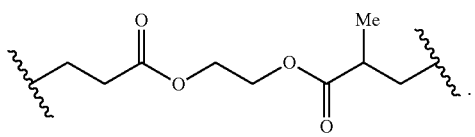 [SMILES: *CCC(=O)OCCOC(=O)C(C)C*]

In some embodiments, the degradable diacyl is further defined as:

In some embodiments, the linker is further defined as:

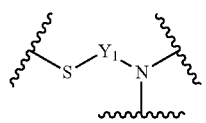
(VI)

wherein:
Y$_1$ is alkanediyl$_{(C\leq 8)}$ or substituted alkanediyl$_{(C\leq 8)}$.

In some embodiments, the delivery lipid nanoparticle composition comprises from about 2.5 to about 40 molar ratio of the cationic ionizable lipid. In some embodiments, the molar ratio of the cationic ionizable lipid is from about 5 to about 30.

In some embodiments, the phospholipid is 1,2-distearoyl-sn-glycero-3-phosphocholine (DSPC) or 1,2-dioleoyl-sn-glycero-3-phosphoethanolamine (DOPE). In one embodiment, the phospholipid is DOPE. In some embodiments, the delivery lipid nanoparticle composition comprises from about 10 to about 45 molar ratio of the phospholipid. In some embodiments, the molar ratio of the phospholipid is from about 20 to about 40.

In some embodiments, the steroid is cholesterol. In some embodiments, the delivery lipid nanoparticle composition comprises from about 15 to about 50 molar ratio of the steroid. In some embodiments, the molar ratio of the steroid is from about 25 to about 50.

In some embodiments, the PEGylated lipid comprises a PEG component from about 1000 to about 10,000 daltons. In some embodiments, the PEG lipid is a PEGylated diacylglycerol. In other embodiments, the PEG lipid is further defined by the formula:

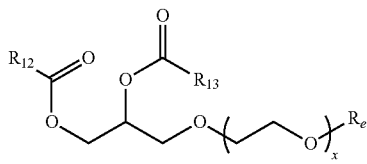

wherein:
R$_{12}$ and R$_{13}$ are each independently alkyl$_{(C\leq 24)}$, alkenyl$_{(C\leq 24)}$, or a substituted version of either of these groups;
R$_e$ is hydrogen, alkyl$_{(C\leq 8)}$, or substituted alkyl$_{(C\leq 8)}$; and
x is 1-250.

In some embodiments, the PEG lipid is dimyristoyl-sn-glycerol or a compound of the formula:

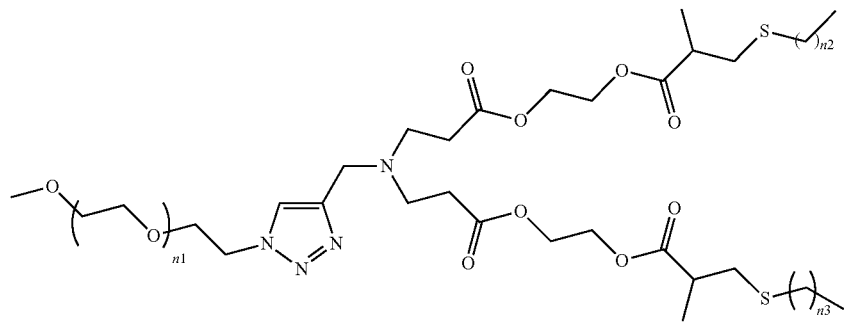

wherein:
n$_1$ is 5-250; and
n$_2$ and n$_3$ are each independently 2-25.

In some embodiments, the delivery lipid nanoparticle composition comprises from about 0.5 to about 10 molar ratio of the PEGylated lipid. In some embodiments, the molar ratio of the PEGylated lipid is from about 1 to about 6.

In yet another aspect, the present disclosure provides compositions comprising:
(A) a nucleic acid, wherein the length is greater than 80 nucleotides; and
(B) a delivery lipid nanoparticle composition:
  (i) from about 5 to about 50 of a cationic ionizable lipid;
  (ii) from about 10 to about 50 of a phospholipid;
  (iii) from about 15 to about 60 of a steroid; and
  (iv) from about 0.25 to about 12.5 of a PEGylated lipid;
  wherein the amounts are as a mole percentage.

In some embodiments, the length of the nucleic acid is from about 90 nucleotides to about 500 nucleotides. In other embodiments, the length of the nucleic acid is from about 1,000 nucleotides to about 7,000 nucleotides. In some embodiments, the nucleic acid is a messenger RNA (mRNA) or a single guide RNA (sgRNA). In some embodiments, the nucleic acid encodes for a protein or a guide for gene editing. In some embodiments, the nucleic acid encodes for or acts in gene editing of a protein that is defective in a disease or disorder.

In some embodiments, the cationic ionizable lipid is a cationic ionizable dendron or a cationic ionizable dendrimer. In some embodiments, the cationic ionizable lipid contains two or more hydrophobic groups, a group which is cationic at physiological pH, a linker group which contains one or more esters. In some embodiments, the cationic ionizable lipid is further defined as a dendron of the formula:

Core-Repeating Unit-Terminating Group (I)

wherein the core is linked to the repeating unit by removing one or more hydrogen atoms from the core and replacing the atom with the repeating unit and wherein: the core has the formula:

(II)

wherein:
X$_1$ is amino or alkylamino$_{(C\leq12)}$, dialkylamino$_{(C\leq12)}$, heterocycloalkyl$_{(C\leq12)}$, heteroaryl$_{(C\leq12)}$, or a substituted version thereof;
R$_1$ is amino, hydroxy, or mercapto, or alkylamino$_{(C\leq12)}$, dialkylamino$_{(C\leq12)}$, or a substituted version of either of these groups; and
a is 1, 2, 3, 4, 5, or 6; or
the core has the formula:

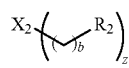
(II)

wherein:
X$_2$ is N(R$_5$)$_y$;
R$_5$ is hydrogen, alkyl$_{(C\leq18)}$, or substituted alkyl$_{(C\leq18)}$; and
y is 0, 1, or 2, provided that the sum of y and z is 3;
R$_2$ is amino, hydroxy, or mercapto, or alkylamino$_{(C\leq12)}$, dialkylamino$_{(C\leq12)}$, or a substituted version of either of these groups;
b is 1, 2, 3, 4, 5, or 6; and
z is 1, 2, 3; provided that the sum of z and y is 3; or
the core has the formula:

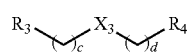
(IV)

wherein:
X$_3$ is —NR$_6$—, wherein R$_6$ is hydrogen, alkyl$_{(C\leq8)}$, or substituted alkyl$_{(C\leq8)}$, —O—, or alkylaminodiyl$_{(C\leq8)}$, alkoxydiyl$_{(C\leq8)}$, arenediyl$_{(C\leq8)}$, heteroarenediyl$_{(C\leq8)}$, heterocycloalkanediyl$_{(C\leq8)}$, or a substituted version of any of these groups;
R$_3$ and R$_4$ are each independently amino, hydroxy, or mercapto, or alkylamino$_{(C\leq12)}$, dialkylamino$_{(C\leq12)}$, or a substituted version of either of these groups; or a group of the formula: —N(R$_f$)$_f$(CH$_2$CH$_2$N)$_e$(R$_c$)R$_d$;
wherein:
e and f are each independently 1, 2, or 3; provided that the sum of e and f is 3;
R$_c$, R$_d$, and R$_f$ are each independently hydrogen, alkyl$_{(C\leq6)}$, or substituted alkyl$_{(C\leq6)}$;
c and d are each independently 1, 2, 3, 4, 5, or 6; or
the core is alkylamine$_{(C\leq18)}$, dialkylamine$_{(C\leq36)}$, heterocycloalkane$_{(C\leq12)}$, or a substituted version of any of these groups;
wherein the repeating unit comprises a degradable diacyl and a linker;
the degradable diacyl group has the formula:

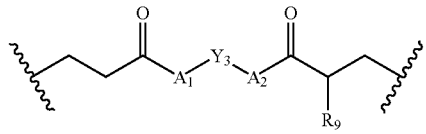
(VII)

wherein:
A$_1$ and A$_2$ are each independently —O— or —NR$_a$—, wherein:
R$_a$ is hydrogen, alkyl$_{(C\leq6)}$, or substituted alkyl$_{(C\leq6)}$;
Y$_3$ is alkanediyl$_{(C\leq12)}$, alkenediyl$_{(C\leq12)}$, arenediyl$_{(C\leq12)}$, or a substituted version of any of these groups; or a group of the formula:

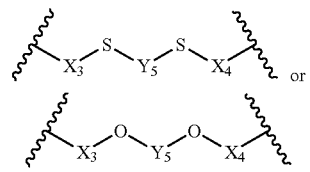
or wherein:
X$_3$ and X$_4$ are alkanediyl$_{(C\leq12)}$, alkenediyl$_{(C\leq12)}$, arenediyl$_{(C\leq12)}$, or a substituted version of any of these groups;
Y$_5$ is a covalent bond, alkanediyl$_{(C\leq12)}$, alkenediyl$_{(C\leq12)}$, arenediyl$_{(C\leq12)}$, or a substituted version of any of these groups; and
R$_9$ is alkyl$_{(C\leq8)}$ or substituted alkyl$_{(C\leq8)}$;
the linker group has the formula:

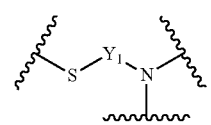
(VI)

wherein:
Y$_1$ is alkanediyl$_{(C\leq12)}$, alkenediyl$_{(C\leq12)}$, arenediyl$_{(C\leq12)}$, or a substituted version of any of these groups; and
wherein when the repeating unit comprises a linker group, then the linker group comprises an independent degradable diacyl group attached to both the nitrogen and the sulfur atoms of the linker group if n is greater than 1, wherein the first group in the repeating unit is a degradable diacyl group, wherein for each linker group, the next repeating unit comprises two degradable diacyl groups attached to the nitrogen atom of the linker group; and wherein n is the number of linker groups present in the repeating unit; and
the terminating group has the formula:

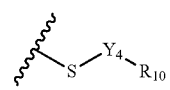
(VIII)

wherein:
Y$_4$ is alkanediyl$_{(C\leq18)}$ or an alkanediyl$_{(C\leq18)}$ wherein one or more of the hydrogen atoms on the alkanediyl$_{(C\leq18)}$ has been replaced with —OH, —F, —Cl, —Br, —I, —SH, —OCH$_3$, —OCH$_2$CH$_3$, —SCH$_3$, or —OC(O)CH$_3$;
R$_{10}$ is hydrogen, carboxy, hydroxy, or aryl$_{(C\leq12)}$, alkylamino$_{(C\leq12)}$, dialkylamino$_{(C\leq12)}$, N-heterocycloalkyl$_{(C\leq12)}$, —C(O)N(R$_{11}$)-alkanediyl$_{(C≤6)}$-heterocycloalkyl$_{(C≤12)}$, —C(O)-alkyl-amino$_{(C≤12)}$, —C(O)-dialkylamino$_{(C≤12)}$, —C(O)—N-heterocyclo-alkyl$_{(C≤12)}$, wherein:

$R_{11}$ is hydrogen, alkyl$_{(C≤6)}$, or substituted alkyl$_{(C≤6)}$;
wherein the final degradable diacyl in the chain is attached to a terminating group;
n is 0, 1, 2, 3, 4, 5, or 6;
or a pharmaceutically acceptable salt thereof.

In some embodiments, the terminating group is further defined by the formula:

$$\text{(VIII)} \quad \xi\text{-S-}Y_4\text{-}R_{10}$$

wherein:
$Y_4$ is alkanediyl$_{(C≤18)}$; and
$R_{10}$ is hydrogen.

In some embodiments, the core is further defined by the formula:

$$\text{(III)} \quad X_2\left(\begin{array}{c}R_2\end{array}\right)_b{}_z$$

wherein:
$X_2$ is $N(R_5)_y$;
$R_5$ is hydrogen or alkyl$_{(C≤8)}$, or substituted alkyl$_{(C≤18)}$; and
y is 0, 1, or 2, provided that the sum of y and z is 3;
$R_2$ is amino, hydroxy, or mercapto, or alkylamino$_{(C≤12)}$, dialkylamino$_{(C≤12)}$, or a substituted version of either of these groups;
b is 1, 2, 3, 4, 5, or 6; and
z is 1, 2, 3; provided that the sum of z and y is 3.

In some embodiments, the core is further defined by the formula:

$$\text{(IV)} \quad R_3\left(\begin{array}{c}\end{array}\right)_c X_3\left(\begin{array}{c}\end{array}\right)_d R_4$$

wherein:
$X_3$ is —$NR_6$—, wherein $R_6$ is hydrogen, alkyl$_{(C≤8)}$, or substituted alkyl$_{(C≤8)}$, —O—, or alkyl-aminodiyl$_{(C≤8)}$, alkoxydiyl$_{(C≤8)}$, arenediyl$_{(C≤8)}$, heteroarenediyl$_{(C≤8)}$, heterocycloalkanediyl$_{(C≤8)}$, or a substituted version of any of these groups;
$R_3$ and $R_4$ are each independently amino, hydroxy, or mercapto, or alkylamino$_{(C≤12)}$, dialkylamino$_{(C≤12)}$, or a substituted version of either of these groups; or a group of the formula: —$N(R_f)(CH_2CH_2N)_e(R_c)R_d$;
wherein:
e and f are each independently 1, 2, or 3; provided that the sum of e and f is 3;
$R_c$, $R_d$, and $R_f$ are each independently hydrogen, alkyl$_{(C≤6)}$, or substituted alkyl$_{(C≤6)}$;
c and d are each independently 1, 2, 3, 4, 5, or 6.

In some embodiments, the core is further defined as:

[Chemical structures shown]

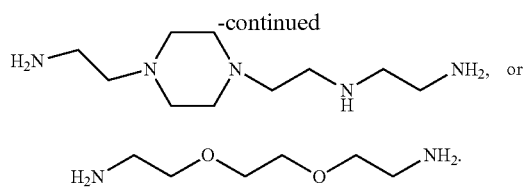

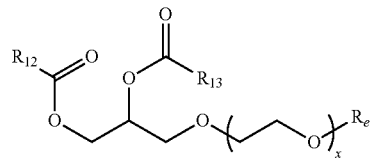

In some embodiments, the degradable diacyl is further defined as:

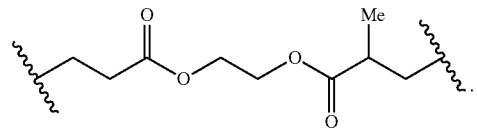

wherein:

$R_{12}$ and $R_{13}$ are each independently alkyl$_{(C\leq24)}$, alkenyl$_{(C\leq24)}$, or a substituted version of either of these groups;

$R_e$ is hydrogen, alkyl$_{(C\leq8)}$, or substituted alkyl$_{(C\leq8)}$; and x is 1-250.

In some embodiments, the PEG lipid is dimyristoyl-sn-glycerol or a compound of the formula:

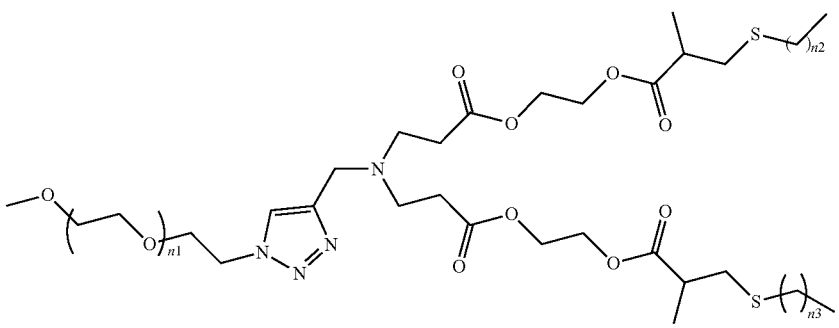

wherein:

$n_1$ is 5-250; and $n_2$ and $n_3$ are each independently 2-25.

In some embodiments, the delivery lipid nanoparticle composition comprises from about 0.5 to about 10 molar percentage of the PEGylated lipid. In some embodiments, the molar percentage of the PEGylated lipid is from about 1 to about 6.

In some embodiments, the composition comprises a weight ratio of the nucleic acid to the cationic ionizable lipid from about 1:1 to about 1:100. In some embodiments, the weight ratio is from about 1:10 to about 1:40 such as from about 1:15 to about 1:25.

In some embodiments, the composition is formulated as a pharmaceutical composition and further comprises an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the composition is formulated for intraarterial or intravenous administration. In some embodiments, the composition is formulated as a unit dose.

In some embodiments, the linker is further defined as:

(VI)

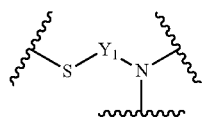

wherein:

$Y_1$ is alkanediyl$_{(C\leq8)}$ or substituted alkanediyl$_{(C\leq8)}$.

In some embodiments, the delivery lipid nanoparticle composition comprises from about 5 to about 40 molar percentage of the cationic ionizable lipid. In some embodiments, the molar percentage of the cationic ionizable lipid is from about 5 to about 30.

In some embodiments, the phospholipid is 1,2-distearoyl-sn-glycero-3-phosphocholine (DSPC) or 1,2-dioleoyl-sn-glycero-3-phosphoethanolamine (DOPE). In one embodiment, the phospholipid is DOPE. In some embodiments, the delivery lipid nanoparticle composition comprises from about 10 to about 45 molar percentage of the phospholipid. In some embodiments, the molar percentage of the phospholipid is from about 20 to about 40.

In some embodiments, the steroid is cholesterol. In some embodiments, the delivery lipid nanoparticle composition comprises from about 15 to about 50 molar percentage of the steroid. In some embodiments, the molar percentage of the steroid is from about 25 to about 50.

In some embodiments, the PEGylated lipid comprises a PEG component from about 1000 to about 10,000 daltons. In some embodiments, the PEG lipid is a PEGylated diacylglycerol. In other embodiments, the PEG lipid is further defined by the formula:

In still yet another aspect, the present disclosure provides methods of treating a disease or disorder in a patient comprising administering a therapeutically effective amount of a composition described herein, wherein the nucleic acid is effective to treat the disease or disorder. In some embodiments, the disease or disorder is a genetic disorder such as diseases or disorders associated with a protein mutation. In some embodiments, the methods further comprise administering a second therapy to the patient. In some embodiments, the methods further comprise administering the composition to the patient once. In other embodiments, the methods further comprise administering the composition to the patient two or more times. In some embodiments, the methods comprise administering the composition to the patient for a time period of greater than 6 months such as from 6 months to 5 years.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. This invention may be better understood by reference to one or more of these drawings in combination with the detailed description of the specific embodiments presented herein.

The patent or application file contains at least one drawing executed in color. Copies of this patent or patent application publication with color drawing(s) will be provided by the Office upon request and payment of the necessary fee.

(FIG. 1A) Design of Experiment (DOE) calculations minimized the number of formulations needed to improve formulation molar ratios. A L16 ($4^4$) orthogonal table design was employed to guide further optimization across two rounds of screening. (FIG. 1B) Red bars highlight more effective DLNPs with a lower fraction of ionizable cationic lipid. (FIG. 1C) Yellow bars highlight the loss of activity when no DMG-PEG was included. See FIG. 2 for molar ratios and molar percentages used in each of the 32 formulations.

FIGS. 2A & 2B. Details of Library A and Library B. Details include determinate molar ratio and percentage of each component, and weight ratio of 5A2-SC8 to mRNA. Physical characteristics such as Z-average size (diameter), PDI, and zeta-potential (surface charge) for all tested (44) DLNP/mRNA formulations in library A, B and C are shown in FIG. 2B.

FIGS. 3A & 3B. The delivery trend for each component in Library A and Library B. These results were used to determine optimal adjustments to improve mRNA delivery.

(FIG. 5A) Formulation details and (FIG. 5B) C57BL/6 mice were randomly grouped and injected IV with 0.25 mg/kg Luc mRNA (n=2). Luminescence was quantified 24 hours after injection.

FIGS. 6A-6E. Characterization of the optimized mDLNP formulation revealed physical attributes amendable to clinical translation. (FIG. 6A) Characterization of the optimized mDLNP formulation revealed physical attributes amendable to clinical translation. Standard siRNA formulations were significantly less efficacious in vivo for delivery of mRNA than optimized mDLNP formulations. (FIG. 6A) Table showing the detailed molar ratios between each component, weight ratio of 5A2-SC8 to mRNA, encapsulation efficiency, pKa, size, and zeta-potential. (FIG. 6B) The morphology of mDLNPs is shown in the TEM image (scale bar=200 nm). (FIG. 6C) DLNP stability was monitored by DLS (n=3) for one week. (FIGS. 6D & 6E) mDLNPs containing DOPE were more efficacious than mDLNPs containing DSPC and the starting siRNA DLNPs. Ex vivo bioluminescence images following at 0.1 and 0.5 mg/kg (I.V.) are shown (n=2). The green triangle denotes detector saturation. The average luminescence for the whole livers was plotted (FIG. 6E).

(FIG. 8A) Time-dependent Luc expression in C57BL/6 mice following IV injection of 0.25 mg/kg Luc mRNA in mDLNPs. Luminescence was recorded at various time-points within 48 h (n=2). (FIG. 8B) For dose-dependent Luc mRNA expression, C57BL/6 mice were injected IV with the doses of 0.05, 0.1, or 0.2 mg/kg. Luminescence was detected 6 h post injection (n=2). (FIG. 8C) Confocal images of mCherry expression in liver cryo-sections following IV injection of 0.5 mg/kg mCherry mRNA (6 h, nuclei are blue, mCherry protein is red, scale bar=50 μm). (FIG. 8D) In vivo transfection efficacy of hepatocytes detected by flow cytometry. C57BL/6 mice were injected with mCherry mDLNPs at a dose of 0.5 mg/kg. Primary hepatocytes were isolated after 6 h and analyzed by flow cytometry.

(FIG. 9A) For time-dependent Luc mRNA expression, C57BL/6 mice were injected IV with the dose of 0.25 mg/kg and luminescence was recorded at various time-points within 48 hours (n=2). (FIG. 9B) For dose-dependent Luc mRNA expression, C57BL/6 mice were injected IV with the doses of 0.05, 0.1 and 0.2 mg/kg, respectively, luminescence was detected at 6 hours post injection (n=2).

(FIG. 12A) Scheme of therapeutic regimen. (FIG. 12B) Immunofluorescence (IF) images of liver sections following injection of FAH mRNA in mDLNPs (10 μg mRNA per mouse, 6 h, scale bar=250 μm). (FIG. 12C) Body weight of FAH−/− mice were monitored in a one month therapy study. Mice (off NTBC water, 2♂, 1♀, n=3) were randomly grouped and injected with PBS, mCherry mDLNPs, or FAH mDLNP every three days (denoted by arrows) until day 30 (10 μg mRNA per injection or about 0.35 mg/kg). At the end point for each mouse, western blot (FIG. 12D) of liver tissue and (FIG. 12E) liver damage markers (TBIL, ALT and AST) were measured to evaluate the therapeutic effects. Not significant: P>0.05.* denotes P<0.05.

(FIG. 16A) Details of formulations tested. (FIG. 16B) Whole animal bioluminescence images following at 0.1 and 0.5 mg/kg (I.V.) are shown (n=2).

DESCRIPTION OF ILLUSTRATIVE EMBODIMENTS

Figures 1A, 1B, 1C:
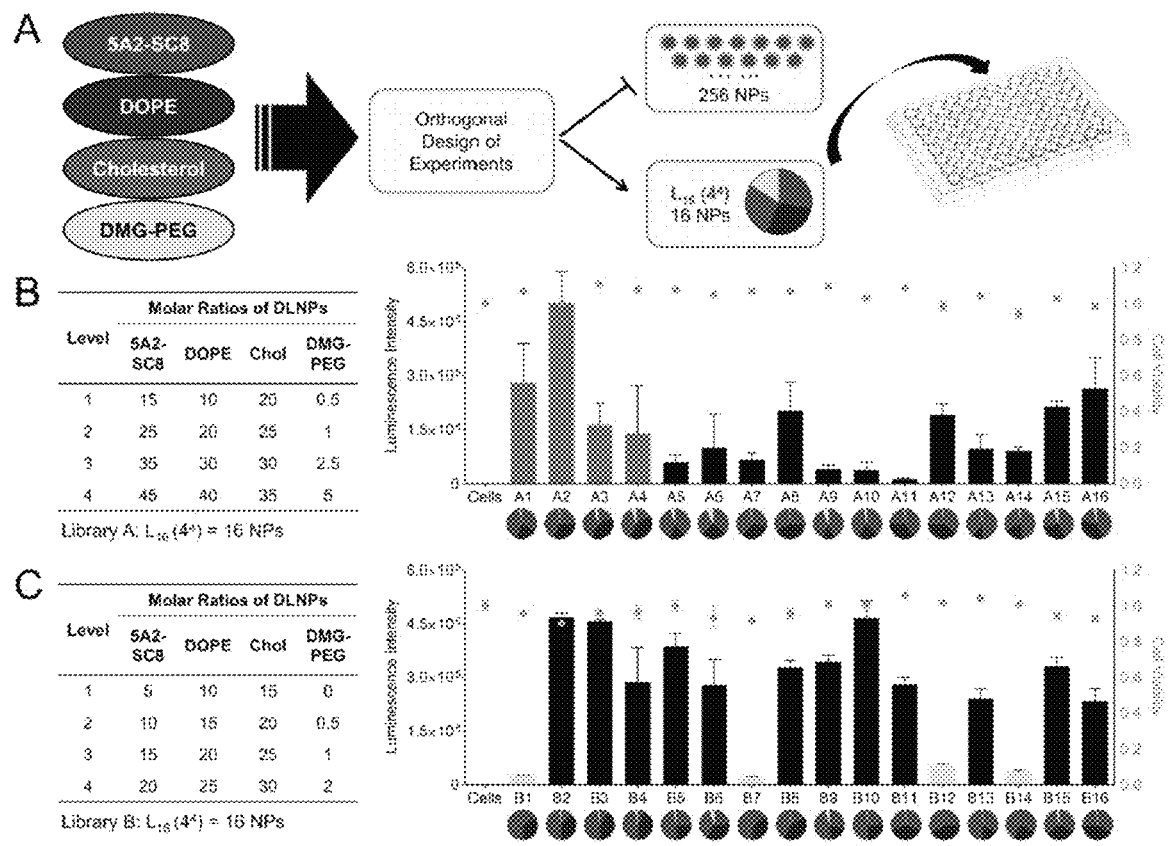
FIGS. 1A-1C. Optimization of DLNPs for mRNA delivery revealed insights into required internal charge balance for efficacious mRNA delivery. IGROV-1 cells were treated with various DLNP formulations containing Luc mRNA (25 ng mRNA per well; 96-well plate (n=4)). Luminescence intensity and cell viability were quantified 24 hours after transfection.

In some aspects, the present disclosure provides lipid nanoparticle compositions for use in the delivery of large nucleic acids such as mRNA. Without wishing to be bound by any theory, it is believed that larger nucleic acids may require different compositions containing different components from smaller nucleic acids such as siRNAs and require smaller amounts of the cationic ionizable lipids. These compositions may be used to treat diseases and disorders for which an mRNA or other large nucleic acids would be useful.

A. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⸺" represents a single bond or a double bond. Thus, for example, the formula

includes

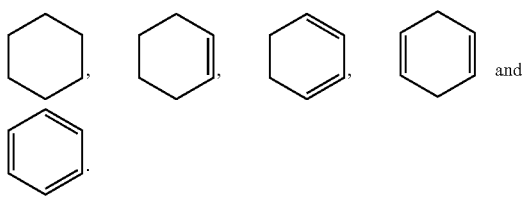

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄", means a single bond where the group attached to the thick end of the wedge is "out of the page." The symbol "⫼⫼⫼", means a single bond where the group attached to the thick end of the wedge is "into the page". The symbol "⌇⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

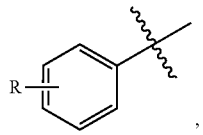

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

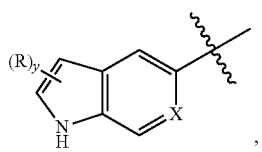

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$," the class "alkene$_{(C≤8)}$," is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl) phenyl, —$C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

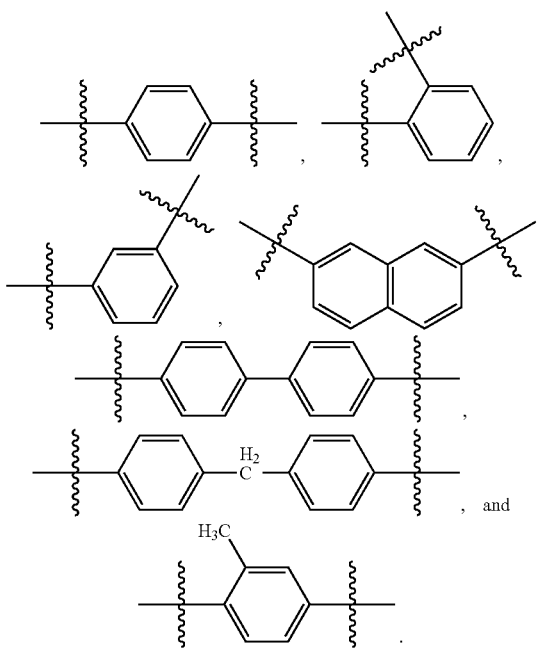

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "aralkyl" when used without the "substituted" modifier refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from are nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

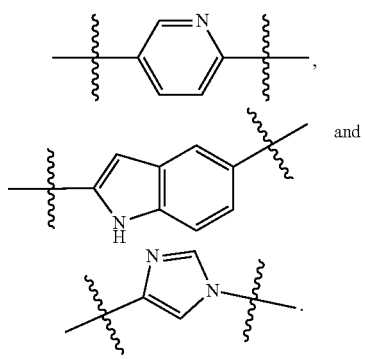

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxctanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

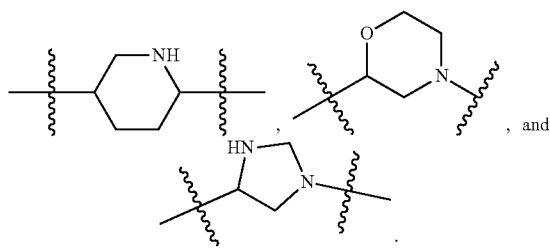

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), C(O)CH$_2$CH$_3$, —C(O)CH$_2$CH$_2$CH$_3$, —C(O)CH(CH$_3$)$_2$, —C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "alkylaminodiyl" refers to the divalent group —NH-alkanediyl-, —NH-alkanediyl-NH—, or -alkanediyl-NH-alkanediyl-. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl) benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc. Within the context of the dendrimer, the repeating unit may also be described as the branching unit, interior layers, or generations. Similarly, the terminating group may also be described as the surface group.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. CATIONIC IONIZABLE LIPIDS

In some aspects of the present disclosure, composition containing compounds containing lipophilic and cationic components, wherein the cationic component is ionizable, are provided. In some embodiments, these cationic ionizable lipids are dendrimers, which are a polymer exhibiting regular dendritic branching, formed by the sequential or generational addition of branched layers to or from a core and are characterized by a core, at least one interior branched layer, and a surface branched layer. (See Petar R. Dvornic and Donald A. Tomalia in Chem. in Britain, 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to described compounds described herein which have a dendron like appearance (e.g. molecules which radiate from a single focal point).

While dendrimers are polymers, dendrimers may be preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bio-attachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol.

Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some aspects, the dendrimers that may be used in the present compositions are assembled using the differential reactivity of the acrylate and methacrylate groups with amines and thiols. The dendrimers may include secondary or tertiary amines and thioethers formed by the reaction of an acrylate group with a primary or secondary amine and a methacrylate with a mercapto group. Additionally, the repeating units of the dendrimers may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine ($—NH_2$) or a carboxylic acid ($—CO_2H$). In still other embodiments, the terminating group is an aliphatic or aromatic group containing one or more hydrogen bond donors such as a hydroxide group, an amide group, or an ester.

The cationic ionizable lipids of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Cationic ionizable lipids may occur as racemates and racemic mixtures, single enantiomers, diastereomeric mixtures and individual diastereomers. In some embodiments, a single diastereomer is obtained. The chiral centers of the cationic ionizable lipids of the present disclosure can have the S or the R configuration. Furthermore, it is contemplated that one or more of the cationic ionizable lipids may be present as constitutional isomers. In some embodiments, the compounds have the same formula but different connectivity to the nitrogen atoms of the core. Without wishing to be bound by any theory, it is believed that such cationic ionizable lipids exist because the starting monomers react first with the primary amines and then statistically with any secondary amines present. Thus, the constitutional isomers may present the fully reacted primary amines and then a mixture of reacted secondary amines.

Chemical formulas used to represent cationic ionizable lipids of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The cationic ionizable lipids of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the cationic ionizable lipids of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a cationic ionizable lipids provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. ADDITIONAL LIPIDS IN THE LIPID NANOPARTICLES

In some aspects of the present disclosure, compositions containing one or more lipids are mixed with the cationic ionizable lipids to create a composition. In some embodiments, the polymers are mixed with 1, 2, 3, 4, or 5 different types of lipids. It is contemplated that the cationic ionizable lipids can be mixed with multiple different lipids of a single type. In some embodiments, the cationic ionizable lipids compositions comprise at least a steroid or a steroid derivative, a PEG lipid, and a phospholipid.

1. Steroids and Steroid Derivatives

In some aspects of the present disclosure, the cationic ionizable lipids are mixed with one or more steroid or a steroid derivative to create a composition. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula below:

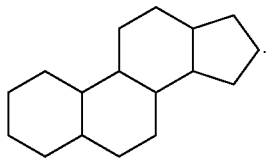 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

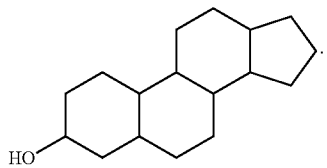 [SMILES: OC1CCC2C(CCC3C4CCCC4CCC23)C1]

In some embodiments of the present disclosure, the steroid or steroid derivative is a cholestane or cholestane derivative. In a cholestane, the ring structure is further defined by the formula:

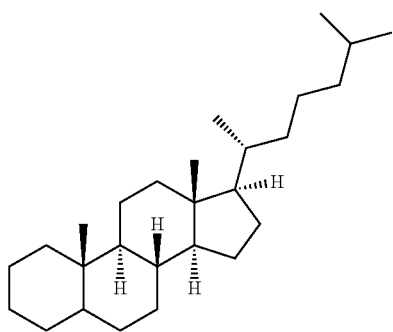

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestere and a sterol or a derivative thereof.

In some embodiments, the compositions may further comprise a molar ratio of the steroid to the cationic ionizable lipids from about 1:4 to about 8:1. In some embodiments, the molar ratio is from about 1:4, 1:3, 1:2, 1:1, 2:1, 3:1, 4:1, 5:1, 6:1, 7:1, to about 8:1 or any range derivable therein. In some embodiments, the molar ratio is from about 1:1 to about 6:1 such as 2:1 or 3:1.

2. PEG or PEGylated Lipid

In some aspects of the present disclosure, the polymers are mixed with one or more PEGylated lipids (or PEG lipid) to create a dendrimer composition. In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified In diacylglycerols and dialkylglycerols. some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present invention are taught by U.S. Pat. No. 5,820,873, WO 2010/141069, or U.S. Pat. No. 8,450,298, which is incorporated herein by reference.

In another aspect, the PEG lipid has the formula:

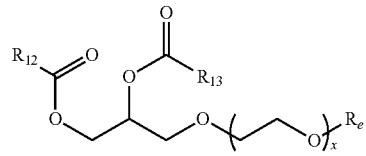

wherein: $R_{12}$ and $R_{13}$ are each independently alkyl$_{(C \leq 24)}$, alkenyl$_{(C \leq 24)}$, or a substituted version of either of these groups; $R_e$ is hydrogen, alkyl$_{(C \leq 8)}$, or substituted alkyl$_{(C \leq 8)}$; and x is 1-250. In some embodiments, $R_e$ is alkyl$_{(C \leq 8)}$ such as methyl. $R_{12}$ and $R_{13}$ are each independently alkyl$_{(C \leq 4\text{-}20)}$. In some embodiments, x is 5-250. In one embodiment, x is 5-125 or x is 100-250.

In some embodiments, the PEG lipid is 1,2-dimyristoyl-sn-glycerol, methoxypolyethylene glycol.

In another aspect, the PEG lipid has the formula:

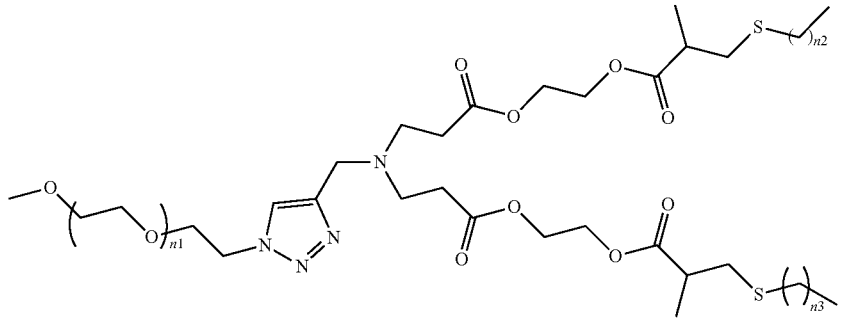

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments, the compositions may further comprise a molar ratio of the PEG lipid to the cationic ionizable lipid from about 1:1 to about 1:100. In some embodiments, the molar ratio is from about 1:1, 3:5, 1:2, 1:5, 1:10, 1:20, 1:30, 1:40, 1:50, 1:60, 1:70, 1:80, 1:90, to about 1:100 or any range derivable therein. In some embodiments, the molar ratio is from about 1:1 to about 1:15.

3. Phospholipid

In some aspects of the present disclosure, the polymers are mixed with one or more phospholipids to create a composition. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or diolcoylphosphatidylethanolamine.

In some embodiments, the compositions may further comprise a molar ratio of the phospholipid to the cationic ionizable lipid from about 1:10 to about 1:20. In some embodiments, the molar ratio is from about 1:5, 2:9, 1:4, 1:2, 8:9, 1:1, 4:3, 2:1, 3:1, 4:1, 6:1, 8:1, to about 10:1 or any range derivable therein. In some embodiments, the molar ratio is from about 1:1 to about 4:1.

D. NUCLEIC ACIDS AND NUCLEIC ACID BASED THERAPEUTIC AGENTS

1. Nucleic Acids

In some aspects of the present disclosure, the dendrimer compositions comprise one or more nucleic acids. In some embodiments, the dendrimer composition comprises one or more nucleic acids present in a weight ratio to the dendrimer from about 5:1 to about 1:100. In some embodiments, the weight ratio of nucleic acid to dendrimer is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any range derivable therein. In some embodiments, the weight ratio is about 1:25 or about 1:7. In addition, it should be clear that the present disclosure is not limited to the specific nucleic acids disclosed herein. The present invention is not limited in scope to any particular source, sequence, or type of nucleic acid, however, as one of ordinary skill in the art could readily identify related homologs in various other sources of the nucleic acid including nucleic acids from non-human species (e.g., mouse, rat, rabbit, dog, monkey, gibbon, chimp, ape, baboon, cow, pig, horse, sheep, cat and other species). It is contemplated that the nucleic acid used in the present disclosure can comprises a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In another embodiment, the nucleic acid is a complementary sequence to a naturally occurring sequence, or complementary to 75%, 80%, 85%, 90%, 95% and 100%. Longer polynucleotides encoding 250, 500, 1000, 1212, 1500, 2000, 2500, 3000 or longer are contemplated herein.

The nucleic acid used herein may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the nucleic acid comprises one or more antisense segments which inhibits expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

2. Modified Nucleobases

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (scc, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In some embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH—CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$)) where each R$_m$ and R$_n$ is, independently, H, an amino protecting group or substituted or unsubstituted C$_1$-C$_{10}$ alkyl.

In some embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In some embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2',4'-(CH$_2$)$_2$-2',4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399, 845); 4'-C(CH$_3$)(CH$_3$)—O-2' and analogs thereof, (see, e.g., WO 2009/006478); 4'-CH$_2$—N(OCH$_3$)-2' and analogs thereof (see, e.g., WO2008/150729); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' and analogs thereof (see, PCT International Application WO 2008/154401).

In some embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl(C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethylencoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl (methyleneoxy) (4'-CH(CH$_3$)—O—2') BNA (also referred to as constrained ethyl or cEt), (G) methylene-thio (4'-CH$_2$S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Methoxy(ethyleneoxy) (4'-CH(CH$_2$OMe)—O—2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129 (26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methylencoxy (4'-CH$_2$—O-2') bicyclic nucleosides have been incorporated into antisense oligonucleotides that showed antisense activity (Frieden et al., Nucleic Acids Research, 2003, 21, 6365-6372).

In some embodiments, substituted sugar moieties comprise one or more non-bridging sugar substituent and one or more bridging sugar substituent (e.g., 5'-substituted and 4'-2' bridged sugars; PCT International Application WO 2007/134181, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfer, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position (sec, e.g., published U.S. Patent Application US 2005/0130923) and/or the 5' position. By way of additional example, carbocyclic bicyclic nucleosides having a 4'-2' bridge have been described (scc, e.g., Freier et al., Nucleic Acids Research, 1997, 25 (22), 4429-4443 and Alback et al., J. Org. Chem., 2006, 71, 7731-7740).

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In some embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In some embodiments, at least one of q$_1$, q$_2$, q$_3$, q$_4$, q$_5$, q$_6$ and q$_7$ is methyl. In some embodiments, THP nucleosides of Formula VII are provided wherein one of R$_1$ and R$_2$ is F. In certain embodiments, R$_1$ is fluoro and R$_2$ is H, R$_1$ is methoxy and R$_2$ is H, and R$_1$ is methoxyethoxy and R$_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO 2008/101157 for other disclosed 5',2'-bis substituted nucleosides) and replacement of the ribosyl ring oxygen atom with S and further substitution at the 2'-position (see U.S. Patent Publication US 2005/0130923) or alternatively 5'-substitution of a bicyclic nucleic acid (see PCT International Application WO 2007/134181 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (sec, e.g., Srivastava et al., 2007).

In some embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In some embodiments, oligonucleotides comprise one or more RNA-like nucleosides. In some embodiments, oligonucleotides comprise one or more DNA-like nucleotides.

In some embodiments, nucleosides of the present invention comprise one or more unmodified nucleobases. In certain embodiments, nucleosides of the present invention comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., 1991; and those disclosed by Sanghvi, Y. S., 1993.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In some embodiments, the present invention provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or(S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., 1989), cholic acid (Manoharan et al., 1994), a thiocther, e.g., hexyl-5-tritylthiol (Manoharan et al., 1992; Manoharan et al., 1993), a thiocholesterol (Oberhauser et al., 1992), an aliphatic chain, e.g., dodecandiol or undecyl residues (Saison-Behmoaras et al., 1991; Kabanov et al., 1990; Svinarchuk et al., 1993), a phospholipid, e.g., di-hexadecyl-rac-glycerol or tricthylammonium 1,2-di-O-hexadecyl-rac-glycero-3-H-phosphonate (Manoharan et al., 1995; Shea et al., 1990), a polyamine or a polyethylene glycol chain (Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

E. KITS

The present disclosure also provides kits. Any of the components disclosed herein may be combined in the form of a kit. In some embodiments, the kits comprise a composition as described above or in the claims.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the lipid nanoparticle components are combined in a single container. In other embodiments, some or all of the lipid nanoparticle components are provided in separate containers.

The kits of the present invention also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Materials and Methods

A. Materials

The dendrimer 5A2-SC8 was synthesized as described previously (Zhou et al., 2016). 1,2-dioleoyl-sn-glycero-3-phosphoethanolamine (DOPE) was purchased from Avanti Polar Lipids. Cholesterol was purchased from Sigma-Aldrich. 1,2-Dimyristoyl-sn-glycerol-methoxypolyethylene glycol 2000 (DMG-PEG) was purchased from NOF America Corporation. The ONE-Glo+Tox Luciferase Reporter assay kit was purchased from Promega Corporation. 4′,6-Diamidino-2-phenylindole dihydrochloride (DAPI), Lysotracker Green DND-26, Hoechst 33342, DLS Ultramicro cuvettes, and Lab-Tek chambered cover glass units were purchased from Thermo Fisher Scientific. Nitisinone (NTBC) was purchased from Yecuris Corporation. Firefly luciferase mRNAs (FLuc mRNA and Cy5-Luc mRNA) were purchased from TriLink BioTechnologies. D-Luciferin (Sodium Salt) was purchased from Gold Biotechnology. Pur-A-Lyzer Midi Dialysis Kits (WMCO, 3.5 kDa) were purchased from Sigma-Aldrich.

B. mRNA Synthesis mCherry mRNA and FAH mRNA used in this work were made by in vitro transcription (IVT). Briefly, coden regions of mCherry and FAH were cloned into pCS2+MT plasmid (Addgene), then 5′, 3′ untranslated regions and polyA were further constructed into a pDNA template, aimed to improve mRNA stability and translation efficiency. Finally, linearized pDNA was performed following IVT protocols (SP6 promoter). The UTP was replaced by N1-methylpseudouridine-5′-triphosphate in the IVT reaction, and Cap-1 mRNA was obtained by Vaccinia Capping Enzyme and 2′-O-methyltransferase (NEB). The coding region sequences for mCherry and FAH were as follows:

```
mCherry (SEQ ID NO: 1):
AUGGUGAGCAAGGGCGAGGAGGAUAACAUGGCCAUCAUCAAGGAGUUCA

UGCGCUUCAAGGUGCACAUGGAGGGCUCCGUGAACGGCCACGAGUUCGA

GAUCGAGGGCGAGGGCGAGGGCCGCCCCUACGAGGGCACCCAGACCGCC

AAGCUGAAGGUGACCAAGGGUGGCCCCCUGCCCUUCGCCUGGGACAUCC

UGUCCCCUCAGUUCAUGUACGGCUCCAAGGCCUACGUGAAGCACCCCGC

CGACAUCCCCGACUACUUGAAGCUGUCCUUCCCCGAGGGCUUCAAUUGG

GAGCGCGUGAUGAACUUCGAGGACGGCGGCGUGGUGACCGUGACCCAGG

ACUCCUCCCUGCAGGACGGCGAGUUCAUCUACAAGGUGAAGCUGCGCGG

CACCAACUUCCCCUCCGACGGCCCCGUAAUGCAGUGUCGUACCAUGGGC

UGGGAGGCCUCCACUGAGCGGAUGUACCCCGAGGACGGCGCCCUGAAGG

GCGAGAUCAAGCAGAGGCUGAAGCUGAAGGACGGCGGCCACUACGACGC

UGAGGUCAAGACCACCUACAAGGCCAAGAAGCCCGUGCAGCUGCCCGGC

GCCUACAACGUCGACAUCAAGUUGGACAUCCUUUCCCACAACGAGGACU

ACACCAUCGUGGAACAGUACGAACGCGCCGAGGGCCGCCACUCCACCGG

CGGCAUGGACGAGCUGUACAAGUAA;

FAH (SEQ ID NO: 2):
AUGUCCUUUAUUCCAGUGGCCGAGGACUCCGACUUUCCCAUCCAAAACC

UGCCCUAUGGUGUUUUCUCCACUCAAAGCAACCCAAAGCCACGGAUUGG

UGUAGCCAUCGGUGACCAGAUCUUGGACCUGAGUGUCAUUAAACACCUC

UUUACCGGACCUGCCCUUUCCAAACAUCAACAUGUCUUCGAUGAGACAA

CUCUCAAUAACUUCAUGGGUCUGGGUCAAGCUGCAUGGAAGGAGGCAAG

AGCAUCCUUACAGAACUUACUGUCUGCCAGCCAAGCCCGGCUCAGAGAU

GACAAGGAGCUUCGGCAGCGUGCAUUCACCUCCCAGGCUUCUGCGACAA

UGCACCUUCCUGCUACCAUAGGAGACUACACGGACUUCUACUCUUCUCG

GCAGCAUGCCACCAAUGUUGGCAUUAUGUUCAGAGGCAAGGAGAAUGCG

CUGUUGCCAAAUUGGCUCCACUUACCUGUGGGAUACCAUGGCCGAGCUU

CCUCCAUUGUGGUAUCUGGAACCCCGAUUCGAAGACCCAUGGGGCAGAU
```

-continued

GAGACCUGAUAACUCAAAGCCUCCUGUGUAUGGUGCCUGCAGACUCUUA

GACAUGGAGUUGGAAAUGGCUUUCUUCGUAGGCCCUGGGAACAGAUUCG

GAGAGCCAAUCCCCAUUUCCAAAGCCCAUGAACACAUUUUCGGGAUGGU

CCUCAUGAACGACUGGAGCGCACGAGACAUCCAGCAAUGGGAGUACGUC

CCACUUGGGCCAUUCCUGGGGAAAAGCUUUGGAACCACAAUCUCCCCGU

GGGUGGUGCCUAUGGAUGCCCUCAUGCCCUUUGUGGUGCCAAACCCAAA

GCAGGACCCCAAGCCCUUGCCAUAUCUCUGCCACAGCCAGCCCUACACA

UUUGAUAUCAACCUGUCUGUCUCUUUGAAAGGAGAAGGAAUGAGCCAGG

CGGCUACCAUCUGCAGGUCUAACUUUAAGCACAUGUACUGGACCAUGCU

GCAGCAACUCACACCACUCUGUUAAUGGAUGCAACCUGAGACCUGGG

GACCUCUUGGCUUCUGGAACCAUCAGUGGAUCAGACCCUGAAAGCUUUG

GCUCCAUGCUGGAACUGUCCUGGAAGGGAACAAAGGCCAUCGAUGUGGG

GCAGGGGCAGACCAGGACCUUCCUGCUGGACGGCGAUGAAGUCAUCAUA

ACAGGUCACUGCCAGGGGACGGCUACCGUGUUGGCUUUGGCCAGUGUG

CUGGGAAAGUGCUGCCUGCCCUUUCACCAGCCUGA.

C. Nanoparticle Formulations

5A2-SC8, DOPE, cholesterol and DMG-PEG were dissolved in ethanol at given molar ratios based on Design of Experiments (DOE). Software called Orthogonal Designing Assistant II V3.1 was used for DOE. mRNA dissolved in citrate buffer (10 mM, pH 4.0), weight ratio of 20:1 (5A2-SC8: mRNA), was pipette mixed rapidly into the lipids solution in ethanol at a volume ratio of 3:1 (mRNA: lipids, v/v), then incubated for 10 min at room temperature. After formation, the fresh DLNP/mRNA formulations were diluted with 1×PBS to 0.5 ng mRNA per L (with ethanol less than 5%) for in vitro assays and size detection. For animal experiments, DLNP/mRNA samples were firstly dialyzed (Pur-A-Lyzer Midi Dialysis Kits, WMCO 3.5 kDa, Sigma-Aldrich) against 1×PBS for 2 h, then diluted with PBS to 15 µl/g to perform intravenous (IV) injection.

D. DLNP Characterization

To evaluate physicochemical properties of mRNA-loaded DLNP formulations, Dynamic Light Scattering (DLS, Malvern; He—Ne laser, λ=632 nm; detection angle=173°) was used. Size distribution and Polydispersity Index (PDI) were measured using 100 µl fresh nanoparticles (0.5 ng mRNA per µl, as described above), followed zeta-potential was tested by diluting with 1×PBS to 800 µl. To calculate encapsulation efficacy of mRNA, the Quant-iT RiboGreen RNA Assay was conducted based on its standard protocol (ThermoFisher) and as previously described. Transmission Electron Microscopy (TEM, FEI Tecnai G2 Spirit Biotwin) was used to observe the DLNP structure. Briefly, 5-8 µL samples (2 mg/mL total lipids) were dropped onto TEM grid for 1 min, and excess sample was wiped away and allowd to dry for 1 h before imaging. To measure the pKa, a modified 2-(p-toluidino)-6-naphthalenesulfonic acid (TNS) assay was employed as previously reported (Zhou et al., 2016). DLNP/mRNA formulations were diluted in a series of buffers containing 10 mM HEPES, 10 mM MES (4-morpholineethanesulfonic acid), 10 mM ammonium acetate and 130 mM NaCl, where the pH ranged from 2.5 to 11. TNS probe (100 µM stock in distilled water) was mixed with above solutions for 5 min with slight shaking, making the final volume of 100 µL that contained total lipids of 60 µM and probe of 2 µM, respectively. The fluorescence of each well was measured by a Tecan plate reader with $\lambda_{Ex}$=321 nm and $\lambda_{Em}$=445 nm and data was normalized to the value of pH 2.5. The pH of half-maximum fluorescence indicated the pKa of formulation.

E. mDLNP Stability

To study mDLNP stability, the sizes and PDI were monitored for one week stored in PBS (4° C. and 37° C.) and in media containing 10% FBS at 37° C. DLNPs were formed as described above and dialyzed with 1×PBS, then were diluted to 5 ng/µL with 1×PBS and 10% FBS (n=3). 160 µL was pipetted into DLS Ultramicro cuvettes and stored at 37° C. Then size and PDI were monitored for one week.

F. In Vitro Luciferase Expression and Cell Viability Tests

Before transfection with luciferase mRNA-loaded DLNP formulations, DOE was performed using the Orthogonal Designing Assistant II V3.1 software. Two rounds of orthogonal assays were conducted using $L_{16}$ ($4^4$) orthogonal tables. IGROV-1 cells were seeded into white 96-well plate with the density of $1 \times 10^4$ cells per well. After 24 h, cells were replaced by 150 µL fresh RPMI 1640 medium (5% FBS), and 50 µL DLNP/Fluc mRNA formulations were added with fixed 25 ng mRNA per well. Cells were further incubated for 24 h and ONE-Glo+Tox kits were used for mRNA expression and cytotoxicity detection based on the standard protocol.

G. Cellular Uptake and Endosomal Escape

Confocal imaging was conducted to study cellular uptake and endosomal escape of DLNP/mRNA formulations. IGROV-1 cells were seeded into Lab-Tek Chambered Coverglass with the density of $2 \times 10^4$ cells per well. After 24 h, cells were replaced by 150 µL fresh RPMI 1640 medium (5% FBS) and treated with 50 µL DLNP/Cy5-Fluc mRNA formulations fixed 50 ng mRNA per well. At 2 h and 8 h after treatment, cells were washed three times with PBS and stained by Lysotracker Green (1:3000 dilution) and Hoechst 33342 (0.1 mg/mL) for 15 min at 37° C., then imaged by confocal microscopy (LSM 700, Zeiss).

H. In Vivo Luc mRNA Delivery

All experiments were approved by the Institution Animal Care and Use Committees of The University of Texas Southwestern Medical Center and were consistent with local, state and federal regulations as applicable. Normal wild-type C57BL/6 mice were purchased from the UTSW mouse breeding core and $FAH^{-/-}$ mice were kindly provided by the laboratory of Professor Hao Zhu. In vivo screening, time- and dose-dependent experiments were evaluated with Luc mRNA delivery. Female C57BL/6 mice, weight of 18-20 g, were injected IV with Luc mRNA formulations at the dose of 0.25 mg/kg, at the given time points, mice were injected intraperitoneal (IP) with D-Luciferin (150 mg/kg) and incubated for 5 min. Luciferase expression of whole body and ex vivo images were imaged by IVIS Lumina system (Perkin Elmer). For dose-dependent Luc mRNA delivery, mice were IV injected with mRNA DLNP (mDLNP) formulations at doses of 0.05 mg/kg, 0.1 mg/kg and 0.2 mg/kg, respectively. After 6 h, luciferase expression was evaluated as described above.

I. In Vivo mCherry mRNA Delivery

Female C57BL/6 mice were injected IV with mCherry mDLNP at a dose of 0.5 mg/kg. After 6 h, mice were sacrificed, and major organs were isolated and imaged by IVIS Lumina system (Perkin Elmer). Isolated liver blocks (1.5 cm×1.5 cm) were embedded into optimal cutting temperature compound (O.C.T.) (Sakura Finetek) and cyro-sectioned (8 µm) using a Cryostat instrument (Leica Biosystems). The sections were stained with 4,6-diamidino-2- phenylindole (DAPI, Vector Laboratories) and observed by confocal microscopy (LSM 700, Zeiss).

J. Flow Cytometry

To study in vivo transfection efficacy of hepatocytes, mCherry mDLNPs were employed. Female C57BL/6 mice were injected IV at the dose of 0.5 mg/kg. After 6 h, primary mouse hepatocytes were isolated by two-step collagenase perfusion. The tubing, perfusion pump, and operating Styrofoam stage was set up. Then the mice were anesthetized by isofluorane, fixed, and the abdomens were cleaned using 70% ethanol. A catheter (BD Insyte IV 24G shielded catheter, connected to liver perfusion medium) was inserted into the inferior vena cava and perfusion was started with liver perfusion medium (Thermo Fisher Scientific, 17701038) with a flow rate of 3 ml/min for 7-10 min, then switched the tubing from liver perfusion medium to liver digestion medium (Thermo Fisher Scientific, 17703034) and continued perfusion for 7-10 min (the same flow rate). The liver was collected into a plate containing 10 mL of liver digestion medium and the liver sac was cut to release the hepatocytes. The released hepatocytes were collected and washed twice with Hepatocyte wash medium (Thermo Fisher Scientific, 17704024) and one more time with 1×PBS. Hepatocytes were further isolated by straining and low speed (50×g) centrifugation. Finally, hepatocytes were analyzed by FACS Aria II SORP machine (BD Biosciences).

K. In Vivo FAH mRNA Therapeutic Study

Before fumarylacetoacetate hydrolase (FAH) mRNA therapy, the quality of FAH mRNA was verified both in vitro and in vivo. A549 cells were selected to evaluate the quality of FAH mRNA. Resultant FAH protein was quantified by western blot. For in vivo evaluation, FAH$^{-/-}$ mice were each injected with FAH mDLNPs containing 10 μg mRNA. After 6 h, liver sections were prepared and immunofluorescence was performed. For FAH mRNA therapy, FAH$^{-/-}$ mice weighing 18-20 g were removed from NTBC (Yecuris) water and marked day 0. The mice were injected with PBS, mCherry mDLNPs (10 μg per mouse) and FAH mDLNPs (10 μg per mouse) every three days until day 30. During this time, the body weight of each mouse was monitored and the mice who lost >20% body weight were euthanized to comply with institutional guidelines on quality of life care. At each endpoint, serum and liver tissues were collected for liver function and western blot analyses, respectively.

L. Immunofluorescence (IF)

To verify the quality of FAH mRNA, FAH$^{-/-}$ were injected by FAH mDLNPs containing 10 μg mRNA per mouse. Six hours later, isolated livers were fixed in 4% paraformaldehyde (PFA) and cryopreserved in optimal cutting temperature compound (O.C.T.). The blocks were cyrosectioned (8 μm) using a Cryostat machine (Leica Biosystems). Then liver sections (8 um) were blocked (5% bovine serum albumin/0.25% Triton X-100) and incubated with primary antibody against FAH (Yecuris, 1:1000). After incubation with fluorophore-conjugated secondary antibodies, sections were counterstained with 4,6-diamidino-2-phenylindole (DAPI) and imaged by inverted microscopy (Leica DMI6000).

M. Liver Function Testing

At each end point, whole blood was collected into BD Microtainer tubes. Serum was separated by centrifuging at the speed of 5000 rpm for 10 min, then Total Bilirubin (TBIL), Alanine Aminotransferase (ALT) and Aspartate Aminotransferase (AST) were tested by the UTSW Molecular Genetics Cores.

N. Protein Extraction

To verify the quality of FAH mRNA, in vitro FAH mRNA mDLNP delivery was performed and western blot assay was used. A549 cells were seeded into 12-well plate with the density of $1\times10^5$ cells per well the day before transfection. Cells were incubated for 24 h with a variety of mDLNP formulations, including Luc mDLNP (1 μg), FAH mDLNP (0.5 μg), FAH mDLNP (1 μg), RNAiMax/FAH mRNA (1 μg) and Lipofectamine2000/ FAH pDNA (0.5 μg). Cells were washed three times with cold 1×PBS, then 100 μL lysis buffer (50 mM Tris HCl, pH 7.4, with 150 mM NaCl, 1 mM EDTA and 1% TRITON X-100) and 1 μL protein inhibitor cocktail (100A, Thermo Fisher) were added. After shaking heavily for 25 min, cell lysates were collected into 1.6 ml tubes and centrifuged for 10 min (13,000 g) at 4° C. Supernatants were collected into new tubes and stored in −80° C. if not used immediately. For protein extraction from tissues, the T-PER tissue protein extraction reagent (ThermoFisher) was used according to the recommended protocol.

O. Western Blot

Protein concentrations were measured by BCA assay kit (ThermoFisher). 15 μg total protein was loaded and separated by 4-20% polyacrylamide gel (ThermoFisher). Separated proteins were transferred into polyvinylidene membrane (BioRad) which was then blocked by 5% BSA (dissolved in PBST) for 1 h at RT. Primary antibodies were applied overnight at 4° C. (rabbit FAH antibody, 1:300 dilution; rabbit beta-actin antibody, 1:2000 dilution). After washing four times using PBST, the membrane was incubated by secondary antibody for 1 h at RT (anti-rabbit IgG, HRP-linked antibody, 1:3000 dilution), and then the membrane treated with ECL substrate (ThermoFisher) and imaged.

P. Statistical Analyses

Data, unless otherwise noted, is reported as mean±S.E.M. Graph Pad Prism version 7 was used to calculate statistical comparisons. Two-tailed Student's t-tests were used to calculate p values. Not significant: $P>0.05$; * denotes $P<0.05$;  denotes $P<0.005$; * denotes $P<0.0005$.

Example 2—Optimization of Molecular Interactions Within DLNPs for Effective mRNA Delivery and Translation To discover non-toxic delivery vehicles that avoid enhancing disease-induced liver dysfunction, a large library of >1,500 ester-based dendrimers containing ionizable amino groups that self-assemble with excipients into DLNPs to effectively deliver siRNAs/miRNAs to compromised livers have been developed (Zhou et al., 2016). To this end, a genetically engineered mouse model of late-stage liver cancer was employed to identify carriers that could balance high delivery potency with low hepatotoxicity to function in mice with severely limited liver function. This led to identification of 5A2-SC8 as a lead lipid dendrimer that could mediate Let-7g miRNA delivery to extend survival. However, it was found that 4-component LNP compositions optimized for small RNAs (cationic ionizable lipid/phospholipid/cholesterol/lipid poly(ethylene glycol) (PEG)=50/10/38/2 (mol/mol)) were not effective for delivering long RNAs. To evaluate the hypothesis that molecular interactions surrounding RNAs in water pockets within LNPs must be critically balanced to enable efficacy of longer RNAs, hybrid lipids called zwitterionic amino lipids (ZALs) that self-assemble into 3-component LNPs without phospholipid were rationally designed, and it was found that they can load, stabilize, and release mRNAs intracellularly with high efficacy (Miller et al., 2017). The fundamental role of each LNP component was further investigated, and it was found that phospholipids mediate RNA loading into LNPs. Studies involving titration of phospholipid into cationic lipid formulations clearly showed that phospholipid was not necessary for siRNA delivery but was required for mRNA delivery (Miller et al., 2017). Increasing phospholipid content progressively improved mRNA loading into the LNP and promoted delivery. Recent reports from other labs on mRNA delivery using LNPs with different phospholipids and compositions further suggests that RNA solubilizing and stabilizing interactions improve LNP organization and increase delivery efficacy (Kauffman et al., 2015; Fenton et al., 2016; Jarzebinska et al., 2016; Kaczmarek et al., 2016; Dong et al., 2016; Li et al., 2016). Since initial ZAL formulations delivered mRNA predominantly to the lungs and DLNPs delivered small RNAs to liver hepatocytes, the inventors sought to use the charge balance knowledge learned from these separate studies to rationally design DLNP carriers for improved mRNA delivery to the liver for HT-1 treatment.

Despite the fundamental evidence that reformulation can increase the ability of LNPs to deliver mRNA, a framework for the rational design of LNPs for long RNAs remains unclear, particularly regarding the roles that each lipid play. To answer these questions and to develop LNPs that can mediate high mRNA delivery for functional protein replacement of FAH, a systematic orthogonal matrix design methodology designed to elucidate functional contributions of each lipid within LNPs for efficacious mRNA delivery was used. 5A2-SC8 was selected as the ionizable cationic dendrimer because it has been successful for siRNA delivery to the liver for investigating gene functionality in cancer development and liver regeneration without concern for material toxicity-induced off-target effects (Zhou et al., 2016; Zhang et al., 2018a; Zhang et al., 2018b). Ionizable cationic lipids are essential for RNA delivery because they bind RNAs at low pH during mixing, and promote intracellular release as the pH decreases during endosomal maturation (Zelphati and Szoca, 1996; Hafez et al., 2001; Sahay et al., 2013; Gilleron et al., 2013; Dahlman et al., 33; Wittrup et al., 2015; Hao et al., 2015; Yan et al., 2016; Yan et al., 2017). 1,2-dioleoyl-sn-glycero-3-phosphoethanolamine (DOPE) was used as the phospholipid due to its productive utility in mRNA formulations (Kauffman et al., 2015; Fenton et al., 2016; Jarzebinska et al., 2016; Kaczmarek et al., 2016; Dong et al., 2016; Li et al., 2016). DOPE enhances RNA loading (Miller et al., 2017) and may form unstable hexagonal phases to aid LNP disassembly and endosome membrane destabilization (Patel et al., 2017; Harvie et al, 1998; Li and Szoka, 2007; Leung et al., 2012; Semple et al., 2010; Cheng and Lee, 2016). Given the previous reports that optimized lipidoid and lipid-like nanoparticles for mRNA delivery, orthogonal experimental design methodologies were applied to 5A2-SC8 dendrimer lipid DLNPs (Kauffman et al., 2015; Li et al., 2015). Without knowing a priori how each component of the LNP should be adjusted, multiple rounds of optimization were used, involving testing 44 DLNPs that cover the theoretical space of >500 formulations. This is important, given that LNPs require a balance of molecular interactions to stabilize long mRNAs where individual parameters may counteract each other. These rounds of library screening (A, B, and C) sequentially improved mRNA delivery.

It has emerged over the past few years that carriers for delivery of small 18-22 base pair siRNAs/miRNAs often require optimization to be able to package and release longer mRNAs effectively. Recent efforts that applied orthogonal experimental design methodologies to empirically optimize lipid and lipid-like nanoparticles for mRNA delivery have highlighted that adjustment of individual LNP components can improve mRNA delivery efficacy (Kauffman et al., 2015 and Li et al., 2015). It has been hypothesized that internal RNA solubilizing and stabilizing interactions improve LNP organization and increase delivery efficacy (Kauffman et al., 2015; Li et al., 2015; Fenton et al., 2016; Jarzebinska et al., 2016; Kaczmarek et al., 2016; Dong et al., 2016; Li et al., 2016; Miller et al., 2017; Yan et al., 2017). For example, hybrid zwitterionic amino lipids (ZALs) have been shown to be able to self-assemble into LNPs without phospholipid to load, stabilize, and release mRNAs intracellular Miller et al., 2017).

Further investigating the fundamental role of each LNP component in a classic 4-component LNP, we realized that phospholipids mediate RNA loading into LNPs. Studies involving titration of phospholipid into cationic lipid formulations clearly showed that phospholipid was not necessary for siRNA delivery but was required for mRNA delivery (Miller et al., 2017). Increasing phospholipid content progressively improved mRNA loading into the LNP and promoted delivery. This prior work has supported our hypothesis that molecular interactions surrounding RNAs in water pockets within LNPs must be critically balanced to enable efficacy of longer RNAs.

Figures 2B, 3A, 3B:
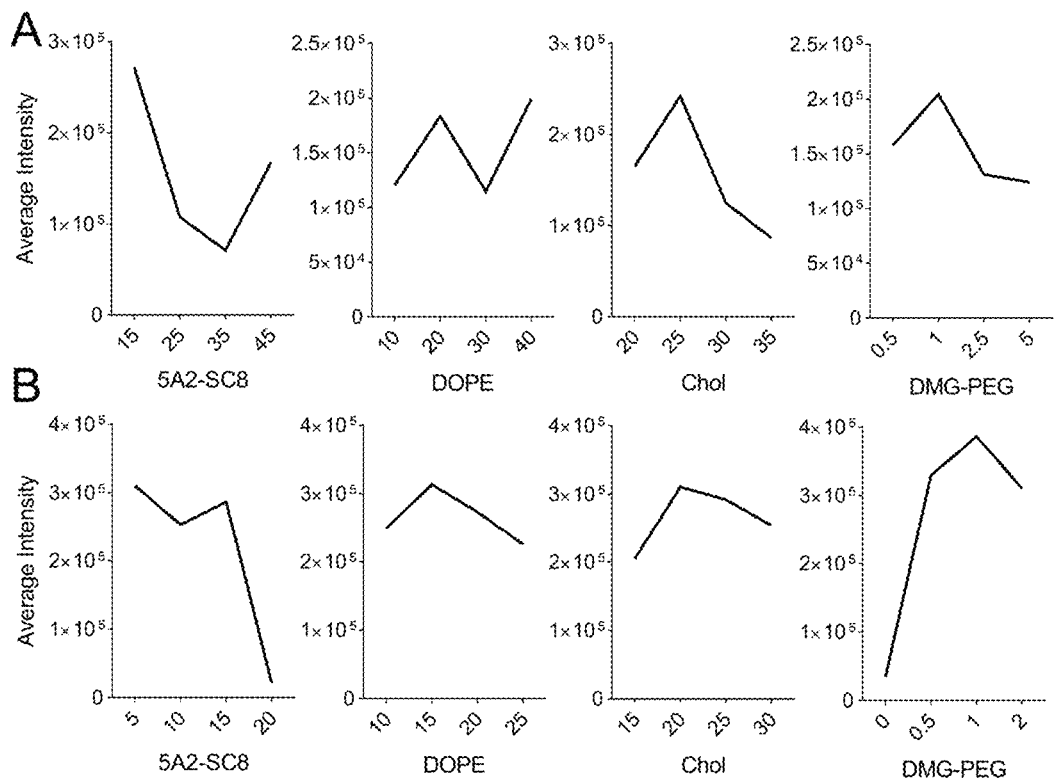

The relative molar ratios of lipids within DLNPs were initially adjusted in the following relative ranges: 5A2-SC8 (15 to 45), DOPE (10 to 40), cholesterol (20 to 35), and DMG-PEG2000 (0.5 to 5.0). Luciferase (Luc) mRNA was used as a reporter sequence to evaluate delivery to IGROV-I ovarian cancer cells in vitro as a representative line with moderate resistance to transfection (FIGS. 1A and 1B). Immediately, it was found that formulations A1-A4 were equal to or more effective than A5-A16. Surprisingly, A1-A4 contain the lowest proportion of ionizable cationic 5A2-SC8 (FIG. 2) (Kaczmarek et al., 2016). Compared to standard siRNA formulations that frequently require 50 mole % of the LNP to be composed of the cationic lipid, the present study found that the cationic lipid can be dramatically decreased for effective mRNA formulations. Moreover, relative increases of zwitterionic DOPE were also advantageous for efficacy (A4, A8, A12, A16). Given that long mRNAs are flexible and present thousands of anionic phosphates per molecule with which to interact with protonated 5A2-SC8 amines at the low pH of mixing, this suggests that these electrostatic interactions cannot be too strong. Instead, a balance of cationic lipids and zwitterionic phospholipids is ideal for association with mRNA solvated with water molecules and salt ions (Leung et al., 2012). In contrast, short siRNAs (only 18-22 base pairs) may resemble rigid rods, where molecular interactions involve hydrophobic forces in addition to weaker electrostatic interactions compared to mRNAs. Thus, initial results from the DLNP optimization revealed that mRNAs may require weaker electrostatic associations, likely to allow for mRNA release after endocytosis. Plotting of this data set as a function of each component revealed a trend for lower ionizable cationic lipid and higher phospholipid (FIG. 3) to maximize activity. No decrease in cellular viability was observed, which was attributed to the low toxicity of the ester-based degradable 5A2-SC8.

The B round of optimization was then focused on proportionally lower 5A2-SC8 (5 to 20) and DOPE (10 to 25) ratios, with higher relative cholesterol (15 to 30) fractions (FIG. 1C). The role of 1,2-dimyristoyl-sn-glycerol-methoxy poly (ethylene glycol) 2000 (DMG-PEG) was also examined. This second round of screening revealed more hits overall, suggesting that the adjustments predicted from Library A were correct. Notably, DLNPs prepared without DMG-PEG (B1, B7, B12, B14) exhibited very low mRNA delivery capability. These results indicate that DMG-PEG is important for DLNP stability.

Figure 4:
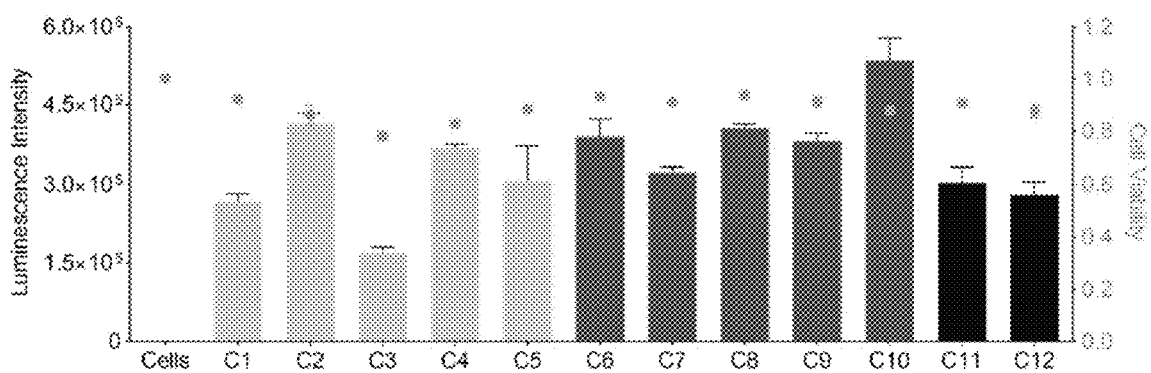
FIG. 4. Optimization of DMG-PEG content and carrier to mRNA weight ratio further improved efficacy. The effects of DMG-PEG percent and weight ratios for mRNA delivery potency were evaluated. The top two formulations (B3 and B10) were selected from Library B and systematically adjusted the DMG-PEG percentage from 1.96% to 4.76%, and the weight ratio of 5A2-SC8 to mRNA from 10/1 to 30/1 to examine the effects on Luc mRNA delivery (25 ng mRNA per well; 96-well plate (n=4)). Luminescence intensity and cell viability were quantified 24 hours after transfection.

Following establishment of optimized formulations that contained significantly decreased 5A2-SC8 and increased DOPE, a third round of DLNPs were created that focused on lead DLNPs B3 and B10, and the effects of PEGylation and carrier: mRNA weight ratio were studied (FIG. 4). In general, a higher weight ratio of 5A2-SC8:mRNA was favorable for delivery, highlighting the important role the ionizable cationic 5A2-SC8 plays for release of mRNA due to its apparent pKa of 6.5 (Zhou et al., 2016). In contrast to optimal siRNA formulations, it was found that mRNA formulations could tolerate higher proportions of DMG-PEG, with the highest efficacy reached at 4.76% (C10). It is conceivable that encapsulation of longer mRNA strands may lead to increased LNP diameters that can be balanced by the smaller size contraction forces of inclusion of more DMG-PEG. Software was then used to predict optimal ratios based on these results (C11, C12). Interestingly, these new DLNPs were less active than the best DLNPs from Library C, suggesting that each of the 5 components in an LNP are not independent variables, as assumed by the software and general intuition. Instead, there is interplay between these factors to construct optimally arranged DLNPs that effectively load mRNA but still retain the ability to release mRNA after endocytosis.

Figures 5A, 5B:
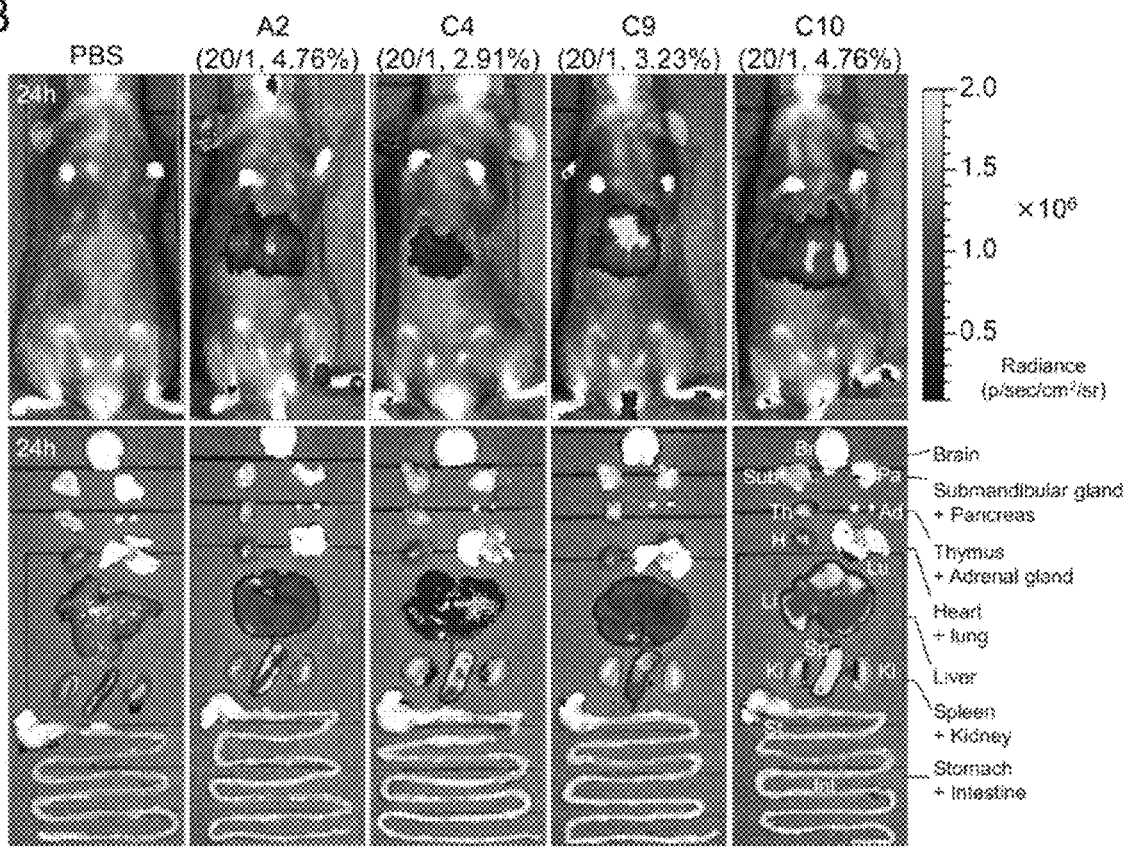
FIGS. 5A & 5B. In vivo screening of Luc mRNA delivery further evaluated the DLNP optimization process. Top formulations (A2, C4, C9 and C10) were examined for their ability to deliver Luc mRNA in vivo.

The top four formulations from all three libraries were evaluated for their ability to deliver Luc mRNA in vivo. All four DLNPs were able to productively deliver Luc mRNA to the liver following intravenous (IV) administration (FIG. 5). Among these, C10 enabled the highest Luc expression in the liver at the tested dose of 0.25 mg/kg. Interestingly, the C4 DLNPs were noticeably less efficacious than the others. The major difference is that C4 has >2-fold less ionizable 5A2-SC8 lipid (9.71 mole %) than the other formulations (~23 mole %). These results indicated that while 5A2-SC8 could be decreased by more than half compared to the fraction in a typical siRNA formulation, it is required for delivery (see FIG. 4 and FIG. 5). From this result, the C10 formulation was selected as the optimal composition for liver delivery of mRNA. Given the large differences from the starting siRNA formulation, the inventors have designated formulation C10 as a messenger RNA optimized DLNP (mDLNP).

Figure 7:
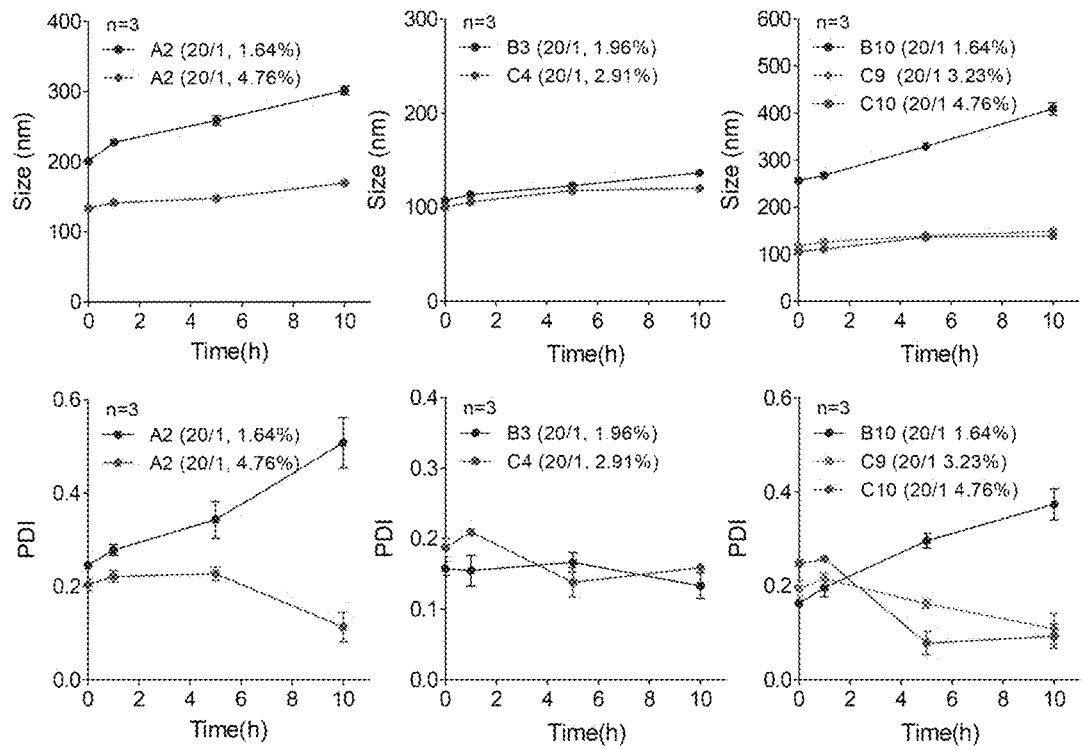
FIG. 7. The comparison of DLNP formulation stability before and after optimization. The top three formulations from Library A (A2) and Library B (B3, B10) were analyzed. The DLS size distribution and polydispersity index (PDI) were monitored for 10 hours.
Figure 15:
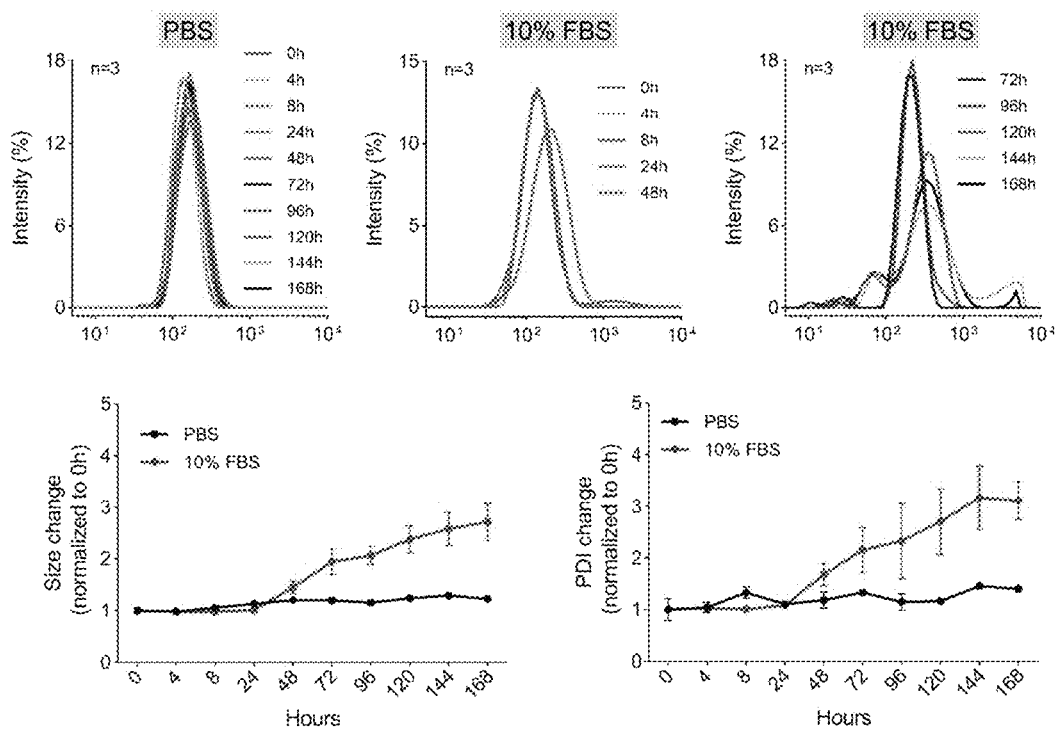
FIG. 15. Uniform diameter and narrow PDI of mDLNPs maintained stability in PBS for >7 days and 2 days challenged in 10% FBS at 37° C. mDLNPs were formed and dialyzed with 1×PBS first, then were diluted to 5 ng/μL with 1×PBS and 10% FBS (n=3). The 160 μdiluted mDLNPs were pipetted into DLS Ultramicro cuvettes and the size and PDI was monitored for one week.
Figures 16A, 16B:
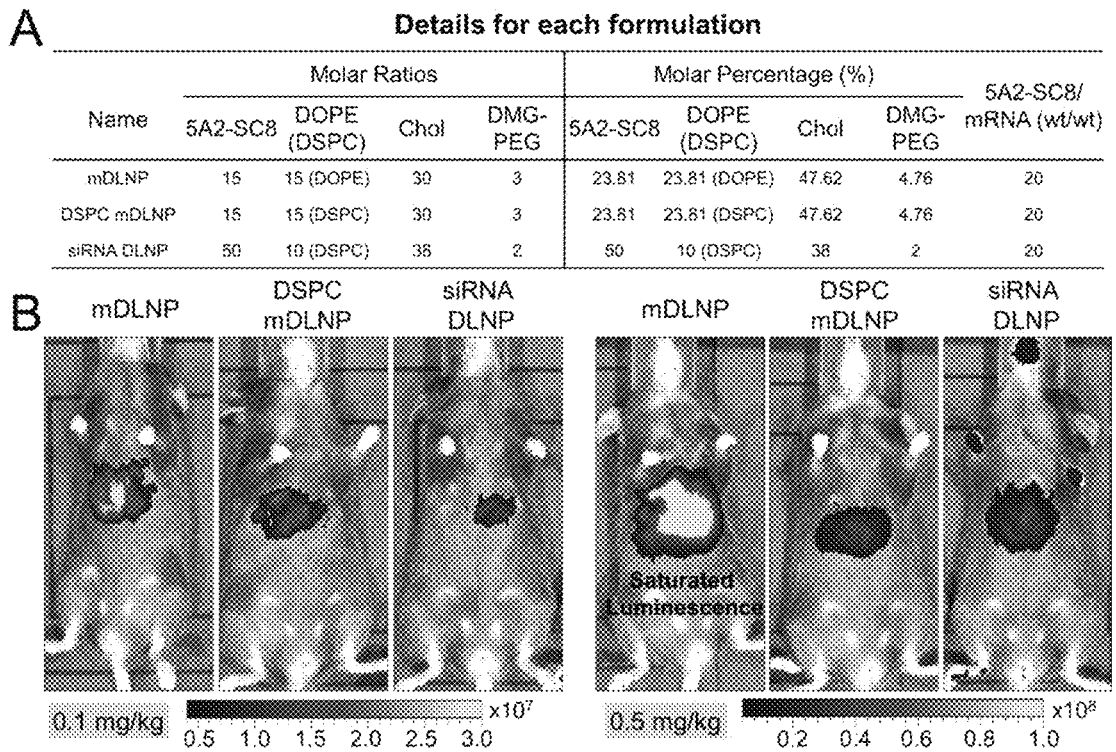
FIGS. 16A & 16B. mRNA-optimized mDLNPs containing DOPE were more efficacious than mDLNPs containing DSPC. mRNA-optimized mDLNPs containing DOPE were also more efficacious than the starting siRNA DLNPs.

Next, physical characterization of mDLNPs was performed (FIG. 6). mDLNPs were monodisperse with a diameter around 100 nm and a near neutral surface charge (−3.58 mV) due to the high amount (4.76%) of DMG-PEG shielding. mDLNPs showed a clear improvement in comparison to initial formulations (FIG. 7). mDLNPs were stable (no change in diameter) over the course of one week of monitoring in PBS at both 4° C. and 37° C. (FIG. 6C and FIG. 15) and for two days under challenging 10% FBS media conditions at 37° C. (FIG. 15). The mDLNPs were stable over the course of one week of monitoring with no change in diameter (FIG. 6C), with a clear improvement in comparison to initial formulations (FIG. 7). Overall, four conclusions have been noted regarding the optimization study comparing an mRNA formulation to an siRNA formulation: 1. The mole fraction of ionizable cationic lipid should be decreased dramatically but not to zero (required for mRNA release); 2. The mole fraction of zwitterionic phospholipid should be increased greatly (aids mRNA loading into DLNPs and augments release); 3. Cholesterol is important for DLNP stability above the ionizable lipid pKa (moderate mole fraction is ideal, efficacy is less sensitive changing cholesterol); and 4. Lipid PEG is required for DLNP stability (mRNA DLNPs can tolerate higher DMG-PEG mole fractions). Additionally, mDLNPs containing more polar phospholipids such as DOPE were more efficacious than mDLNPs containing DSPC and the starting siRNA DLNPs (FIGS. 6D, 6E, and 16). These general design guidelines can likely be applied to other cationic ionizable lipid-based 4 component LNPs (Hajj et al., 2017) to improve mRNA delivery efficacy.

Figures 8A, 8B, 8C, 8D:
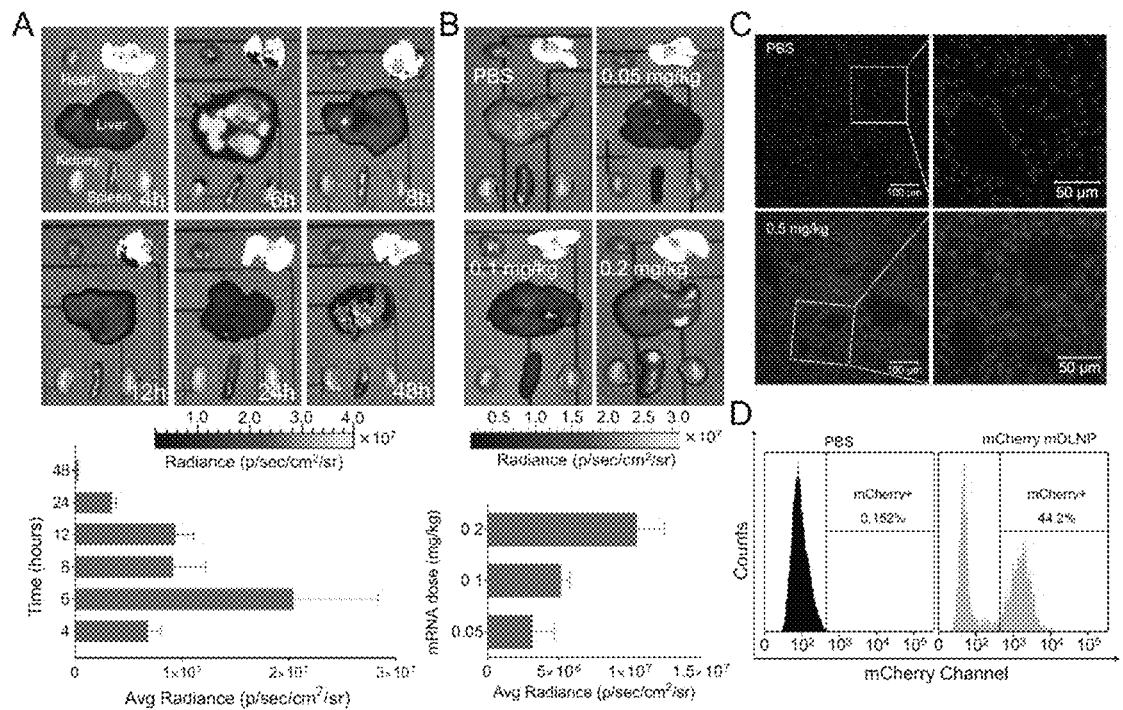
FIGS. 8A-8D. mDLNPs deliver mRNA in a dose-dependent manner with high transfection efficiency of liver hepatocytes.
Figures 9A, 9B:
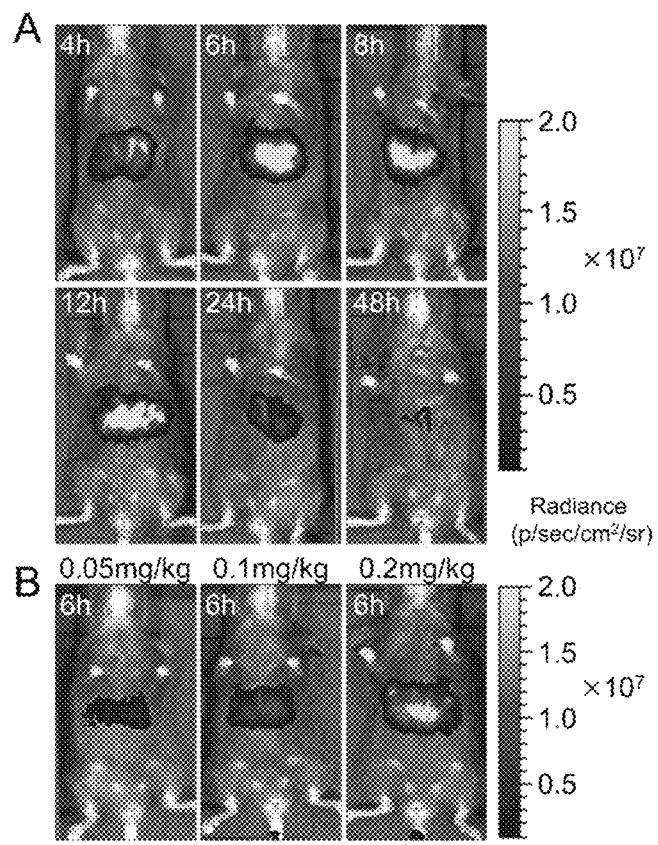
FIGS. 9A & 9B. Whole body luminescence imaging of mice following IV injection of Luc mRNA mDLNPs.
Figure 10:
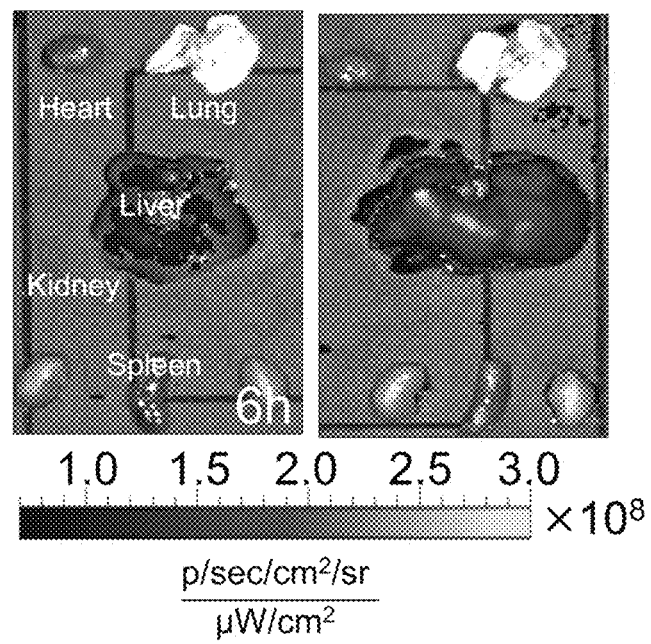
FIG. 10. Ex vivo fluorescence images of mice following IV injection of mCherry mRNA DLNPs. Doses of 0.25 mg/kg (left) and 0.5 mg/kg (right) mRNA DLNPS. 6 hours post injection, mice were sacrificed and major organs were imaged by an IVIS Lumina system.

Example 3—IV Administration of mRNA-Loaded DLNPs Result in Robust, Dose Dependent Protein Activity To further understand mDLNP delivery to the liver, time dependent Luc activity following IV administration was quantified. Luc protein expression peaked at 6 hours post-injection and persisted for about two days at a high level ($10^7$ photons/second, 0.25 mg/kg) at the organ (FIG. 8A) and whole-body level (FIG. 9). Next, the in vivo dose responsive behavior of delivery was examined (FIG. 8B). Luc expression increased with increasing dose from 0.05 mg/kg to 0.2 mg/kg mRNA. Average radianece across the whole livers was calculated and plotted for both the time-dependent and dose response studies (FIGS. 8A & 8B). With expression above $10^6$ photons/second at a 0.05 mg/kg mRNA dose, mDLNPs are likely the most efficacious mRNA carrier reported to date. Next, delivery to liver hepatocytes was quantified. mCherry mRNA was delivered at a dose of 0.5 mg/kg and compared mCherry expression to PBS injected controls by fluorescence imaging of liver sections (FIG. 8C). Strong red mCherry signal was observed throughput the liver (FIG. 10). To further analyze transfection efficiency, hepatocytes were isolated from injected mice and used flow cytometry to quantify mCherry mRNA delivery specifically to hepatocytes. It was found that 44.2% of all hepatocytes were strongly expressing mCherry protein 6 hours following IV administration of mCherry mRNA mDLNPs. Previous work has shown that mutations in FAH have been corrected using CRISPR/Cas components delivered by hydrodynamic injection (Yin et al., 2014 and Pankowicz et al., 2016) or by combining non-viral delivery of Cas9 mRNA with viral delivery of sgRNA and DNA (Yin et al., 2016). Currently, the efficiency of these processes has been very low, reported as 0.4% and 6% of hepatocytes in prior publications (Yin et al., 2014 and Yin et al., Nat. 2016). Without wishing to be bound by any theory, it is believed that protein replacement of FAH via mRNA using optimized mDLNPs is a viable approach due to the high fraction of hepatocytes that express functional protein (>44%).

Figure 11:
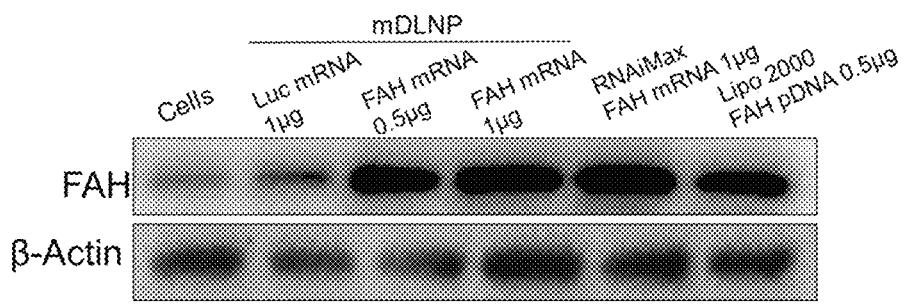
FIG. 11. Western blot of FAH mRNA delivery in A549 cells. To evaluate FAH mRNA quality, A549 cells were seeded in 12-well plate and treated by different formulations. After 24 h, total protein was collected and western blotting was performed.

Recently it has been found that mutations in FAH can been corrected using CRISPR/Cas components delivered by hydrodynamic injection (Yin et al., 2014; Pankowicz et al., 2016) or by combining non-viral delivery of Cas9 mRNA with viral delivery of sgRNA and DNA (Yin et al., 2016). However, the efficiency of these processes has been very low, reported as 0.4% and 6% of hepatocytes in prior publications (Yin et al., 2014; Yin et al., 2016). Therefore, it is hypothesized that protein replacement of FAH via mRNA using optimized mDLNPs offers a therapeutic advantage where >44% of hepatocytes highly express protein. Using multiple rounds of an in vitro/in vivo orthogonal experimental design methodology, a formulation with potential to deliver enough FAH mRNA (FIG. 11) to have a therapeutic benefit in diseased mice was found.

Figures 12A, 12B, 12C, 12D, 12E:
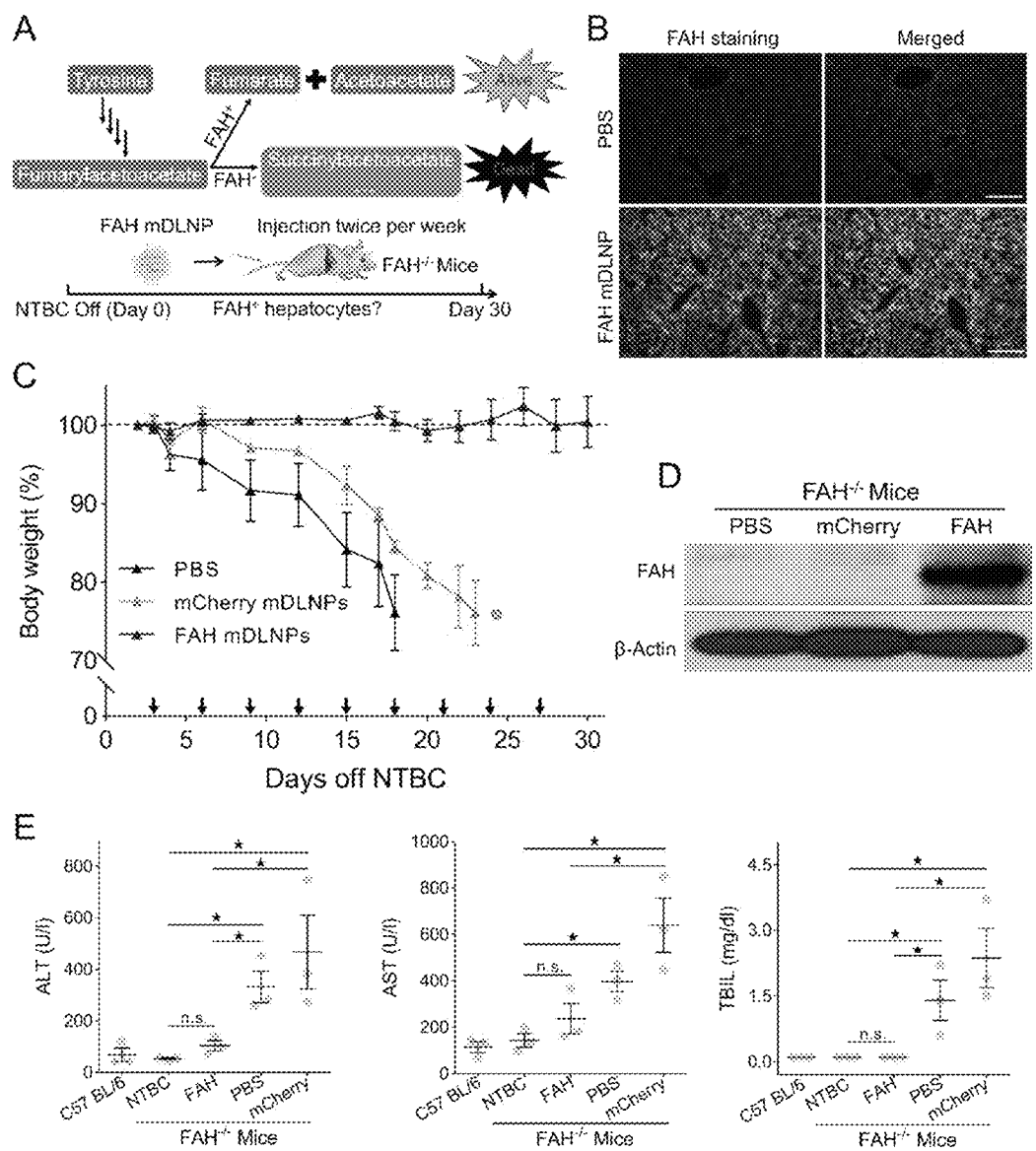
FIGS. 12A-12E. mDLNP delivery of FAH mRNA normalized body weight and liver function in FAH(−/−) mice.
Figure 13:
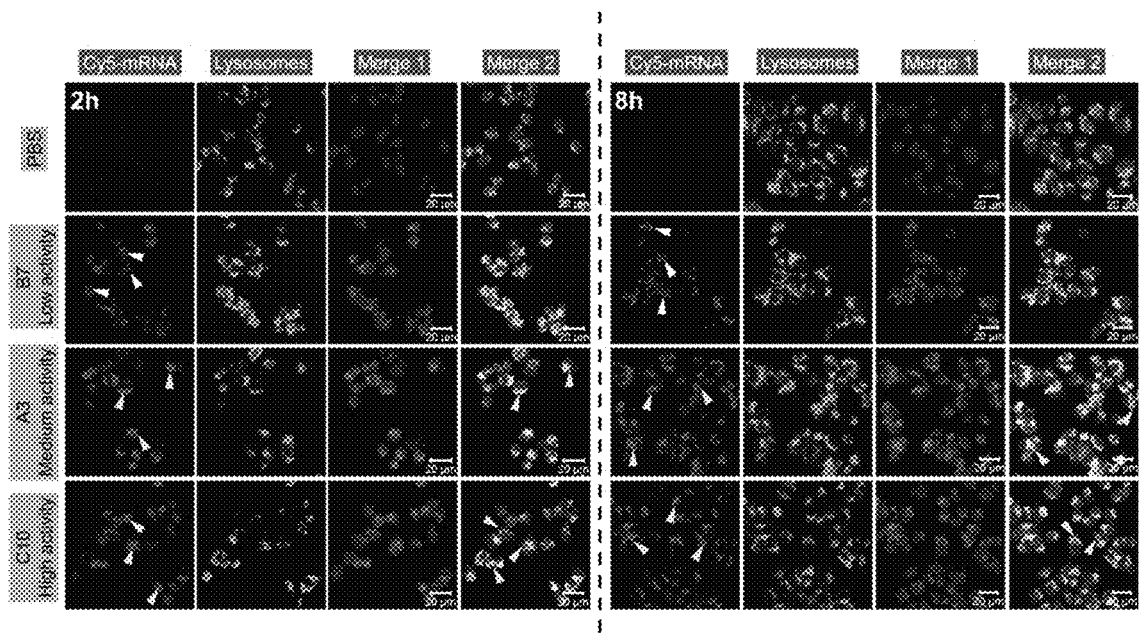
FIGS. 13. A3 and C10 DLNP formulations exhibited greater cellular uptake and endosomal escape than B7 formulation. IGROV1 cells were treated with B7 (low activity), A3 (medium activity) and C10 (high activity) formulations (50 ng Cy5-Luc mRNA) for 2 h and 8 h, then imaged by confocal microscopy. Cy5-labeled mRNA (red), endosomes/lysosomes (green), and nuclei (blue) are shown. Merge 1 combines blue and red. Merge 2 combines blue, red and green. White arrows indicate punctate fluorescence and yellow arrows indicate diffused fluorescence and endosomal escape. Scale bar=20 μm.
Figure 14:
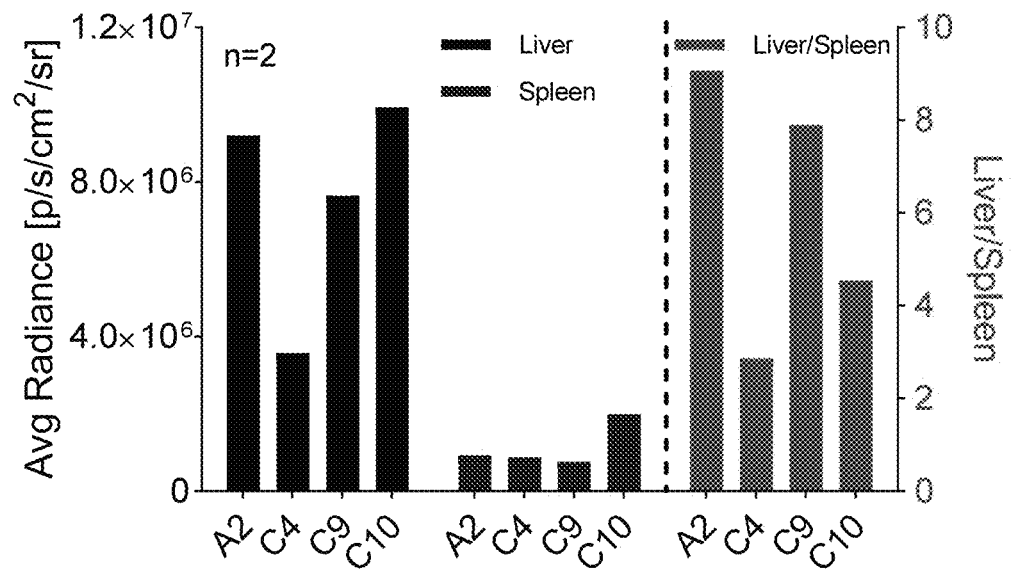
FIG. 14. Quantified luminescence of liver and spleen from A2, C4, C9 and C10 formulations treated mice. A2, C4, C9 and C10 were examined to deliver Luc mRNA in vivo with 0.25 mg/kg Luc mRNA by IV injection (n=2). After 24 h, luminescence of liver and spleen were quantified by IVIS Lumina system.

Example 4—DLNPs Mediate FAH mRNA Delivery to the Livers of FAH$^{-/-}$ Mice to Normalize Body Weight and Liver Function for More Than One Month To evaluate efficacy for FAH protein replacement therapy, a knockout model of HT-1 disease (FAH$^{-/-}$) was employed (Grompe et al., 1995). Therefore, this mouse model is optimal for evaluating protein replacement therapy via mRNA delivery, and less suitable for correction by gene editing These mice are maintained on NTBC to reduce symptoms of HT-1. Following removal of NTBC, FAH$^{-/-}$ mice immediately start to lose body weight, build up toxic levels of metabolites including succinylacetone, and succumb to death from liver failure. After removing FAH$^{-/-}$ mice from NTBC water, mice were treated with IV injections of 10 μg FAH mRNA per mouse every 3 days in mDLNPs (about 0.35 mg/kg) (FIG. 12A). This dose and schedule were selected based mRNA delivery kinetics. The body weight of the mice was monitored for 30 days. PBS injections and mCherry mDLNPs served as controls. First, the ability of mDLNPs to deliver FAH mRNA was evaluated by measuring FAH protein expression in the liver using immunofluorescence staining (FIG. 12B). Strong FAH antibody staining was observed throughout the liver sections. Body weight was measured during the course of the therapeutic regiment. FAH$^{-/-}$ mice injected with PBS or mCherry mRNA control mDLNPs lost more than 20% of their body mass within three weeks. In contrast, FAH$^{-/-}$ mice treated with FAH mRNA mDLNPs were active, healthy, and did not lose any weight at all (FIG. 12C). Survival was extended with continued mRNA treatment. Although the experiment was halted after one month, continued mRNA delivery would likely mediate survival indefinitely.

To confirm that FAH protein production was the cause of increased survival, FAH was detected by western blot from isolated livers (FIG. 12D). Strong FAH protein expression was observed only in the FAH mRNA treated mice. In addition, FAH-mice treated with FAH mRNA mDLNPs had equivalent levels of TBIL, ALT, and AST compared to wild type C57BL/6 mice and FAH$^{-/-}$ mice maintained on NTBC (FIG. 12E). In contrast, FAH$^{-/-}$ mice injected with PBS or mCherry control mDLNPs had elevated liver damage markers. This challenging experiment, performed in FAH$^{-/-}$ mice that harbor compromised livers, demonstrates that 5A2-SC8 mDLNPs have the ability to productively deliver FAH mRNA to hepatocytes to produce therapeutically efficacious levels of FAH protein over an extended period of time. This delivery system therefore has the capability to function in a compromised host with liver disease. The ability to deliver high levels of FAH mRNA to >40% of all hepatocytes to normalize body weight and liver function demonstrates the utility of 5A2-SC8 mDLNPs for treatment of HT-1.

The above experiments provide a non-toxic degradable delivery system optimized for delivery of full length mRNAs to liver hepatocytes. Due to the high in vivo transfection efficiency and efficacy, 5A2-SC8 mDLNPs were able to extend survival in FAH$^{-/-}$ knockout mice suffering from HT-1. FAH mRNA treatment normalized body mass and liver function through the entire 30-day experiment. In the course of this work, it was found that LNPs optimized for mRNA delivery may contain significantly less ionizable cationic lipid and more zwitterionic phospholipids compared to standard siRNA formulations. This work further provides a rational design guideline to redevelop other siRNA-delivering LNPs for delivery of mRNA. Moreover, the capability of 5A2-SC8 mDLNPs to deliver FAH mRNA to diseased livers without any carrier toxicity makes this system suitable for treatment of a wide variety of liver diseases.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,687,808
U.S. Pat. No. 4,587,044
U.S. Pat. No. 4,605,735
U.S. Pat. No. 4,667,025
U.S. Pat. No. 4,762,779
U.S. Pat. No. 4,789,737
U.S. Pat. No. 4,824,941
U.S. Pat. No. 4,828,979
U.S. Pat. No. 4,835,263
U.S. Pat. No. 4,845,205
U.S. Pat. No. 4,876,335
U.S. Pat. No. 4,904,582
U.S. Pat. No. 4,948,882
U.S. Pat. No. 4,958,013
U.S. Pat. No. 5,082,830
U.S. Pat. No. 5,109,124
U.S. Pat. No. 5,112,963
U.S. Pat. No. 5,118,802
U.S. Pat. No. 5,130,302
U.S. Pat. No. 5,134,066
U.S. Pat. No. 5,138,045
U.S. Pat. No. 5,175,273
U.S. Pat. No. 5,214,136
U.S. Pat. No. 5,218,105
U.S. Pat. No. 5,245,022
U.S. Pat. No. 5,254,469
U.S. Pat. No. 5,258,506
U.S. Pat. No. 5,262,536
U.S. Pat. No. 5,272,250
U.S. Pat. No. 5,292,873
U.S. Pat. No. 5,317,098
U.S. Pat. No. 5,367,066
U.S. Pat. No. 5,371,241
U.S. Pat. No. 5,391,723
U.S. Pat. No. 5,414,077
U.S. Pat. No. 5,416,203
U.S. Pat. No. 5,432,272
U.S. Pat. No. 5,451,463

U.S. Pat. No. 5,457,187
U.S. Pat. No. 5,459,255
U.S. Pat. No. 5,484,908
U.S. Pat. No. 5,486,603
U.S. Pat. No. 5,502,177
U.S. Pat. No. 5,510,475
U.S. Pat. No. 5,512,439
U.S. Pat. No. 5,512,667
U.S. Pat. No. 5,514,785
U.S. Pat. No. 5,525,465
U.S. Pat. No. 5,525,711
U.S. Pat. No. 5,541,313
U.S. Pat. No. 5,545,730
U.S. Pat. No. 5,552,538
U.S. Pat. No. 5,552,540
U.S. Pat. No. 5,565,552
U.S. Pat. No. 5,567,810
U.S. Pat. No. 5,574,142
U.S. Pat. No. 5,578,717
U.S. Pat. No. 5,578,718
U.S. Pat. No. 5,580,731
U.S. Pat. No. 5,585,481
U.S. Pat. No. 5,587,371
U.S. Pat. No. 5,587,469
U.S. Pat. No. 5,591,584
U.S. Pat. No. 5,594,121
U.S. Pat. No. 5,595,726
U.S. Pat. No. 5,596,091
U.S. Pat. No. 5,597,696
U.S. Pat. No. 5,599,923
U.S. Pat. No. 5,599,928
U.S. Pat. No. 5,608,046
U.S. Pat. No. 5,614,617
U.S. Pat. No. 5,645,985
U.S. Pat. No. 5,681,941
U.S. Pat. No. 5,688,941,
U.S. Pat. No. 5,750,692
U.S. Pat. No. 5,763,588
U.S. Pat. No. 5,820,873
U.S. Pat. No. 5,830,653
U.S. Pat. No. 6,005,096
U.S. Pat. No. 6,268,490
U.S. Pat. No. 6,506,559
U.S. Pat. No. 6,525,191
U.S. Pat. No. 6,573,099
U.S. Pat. No. 6,670,461
U.S. Pat. No. 6,673,611
U.S. Pat. No. 6,770,748
U.S. Pat. No. 6,794,499
U.S. Pat. No. 7,034,133
U.S. Pat. No. 7,053,207
U.S. Pat. No. 7,399,845
U.S. Pat. No. 8,450,298
U.S. patent application Ser. No. 12/129,154
U.S. Patent Application No. 60/989,574
U.S. Patent Application No. 61/026,995
U.S. Patent Application No. 61/026,998
U.S. Patent Application No. 61/056,564
U.S. Patent Application No. 61/086,231
U.S. Patent Application No. 61/097,787
U.S. Patent Application No. 61/099,844
U.S. Patent Publication No. 2004/0171570
U.S. Patent Publication No. 2002/0168707
U.S. Patent Publication No. 2003/0051263
U.S. Patent Publication No. 2003/0055020
U.S. Patent Publication No. 2003/0159161
U.S. Patent Publication No. 2004/0019001
U.S. Patent Publication No. 2004/0064842
U.S. Patent Publication No. 2004/0171570
U.S. Patent Publication No. 2004/0265839
U.S. Patent Publication No. 2005/0130923
U.S. Patent Publication No. 2007/0287831
U.S. Patent Publication No. 2008/0039618
PCT Application No. PCT/US2008/064591
PCT Application No. PCT/US2008/066154
PCT Application No. PCT/US2008/068922
PCT Publication No. WO 1994/14226
PCT Publication No. WO 2004/106356
PCT Publication No. WO 2005/021570
PCT Publication No. WO 2007/134181
PCT Publication No. WO 2008/101157
PCT Publication No. WO 2008/154401
PCT Publication No. WO 2009/006478
PCT Publication No. WO 2010/141069
Adams et al., BMC Neurol11, 181, 2017.
Akinc et al., A combinatorial library of lipid-like materials for delivery of RNAi therapeutics. Nat. Biotechnol. 26, 561-569, 2008.
Albaek et al., J. Org. Chem., 2006, 71, 7731-7740.
Albertsson and Varma, Adv Polym Sci: 157, 1, 2002.
Ausubel et al., 1994.
Bikard et al., 2013
Bosman et al., About dendrimers: Structure, physical properties, and applications. Chem. Rev. 99, 1665-1688 (1999).
Boyerinas et al., The role of let-7 in cell differentiation and cancer. Endocr.-Relat. Cancer 17, F19-F36 (2010).
Braasch et al., Chem. Biol., 2001, 8, 1-7
Carlmark et al., New methodologies in the construction of dendritic materials. Chem. Soc. Rev. 38, 352-362, 2009.
Chattopadhyaya et al., J. Org. Chem., 2009, 74, 118-134.
Cheng et al., MicroRNA silencing for cancer therapy targeted to the tumour microenvironment. Nature 518, 107-110 (2015).
Cho et al., 2013
Coelho et al., New Engl. J. Med. 369, 819-829, 2013.
Coelho et al., New Engl J Med: 369, 819, 2013.
Crooke et al., J. Pharmacol. Exp. Ther., 277, 923, 1996.
Dahlman et al., Nat Nanotechnol 2014.
Daige et al., Systemic delivery of a miR34a mimic as a potential therapeutic for liver cancer. Mol. Cancer Ther. 13, 2352-2360 (2014).
Davis et al., Evidence of RNAi in humans from systemically administered siRNA via targeted nanoparticles. Nature 464, 1067-1070 (2010).
Davis et al., Nature (London, U. K.): 464, 1067, 2010.
DeRosa et al., Gene Ther. 23, 699-707, 2016.
Dong et al., Nano Lett. 16, 842-848, 2016
Duncan and Izzo, Dendrimer biocompatibility and toxicity. Adv. Drug Deliv. Rev. 57, 2215-2237 (2005).
Elayadi et al., Curr. Opinion Invens. Drugs, 2001, 2, 5561
Englisch et al., Angewandte Chemie, International Edition, 30, 613, 1991.
Fenton et al., Adv. Mater. 28:2939-2943, 2016.
Fenton et al., Adv. Mater. 28, 2939-2943, 2016.
Franc and Kakkar, "Click" methodologies: efficient, simple and greener routes to design dendrimers. Chem. Soc. Rev. 39, 1536-1544, 2010.
Fréchet and Tomalia (eds.) Dendrimers and other dendritic polymers. (John Wiley & Sons, Ltd, New York, USA; 2002).
Freier et al., Nucleic Acids Research, 1997, 25 (22), 4429-4443.
Frieden et al., Nucleic Acids Research, 2003, 21, 6365-6372

Gillies and Frechet, Designing macromolecules for therapeutic applications: Polyester dendrimer-poly (ethylene oxide) "bow-tie" hybrids with tunable molecular weight and architecture. J. Am. Chem. Soc. 124, 14137-14146 (2002).

Grayson and Fréchet, Convergent dendrons and dendrimers: From synthesis to applications. Chem. Rev. 101, 3819-3868 (2001).

Green et al., ACCOUNTS CHEM RES: 41, 749, 2008.

Hajj & Whitehead, Nat. Rev. Mater. 2, 17056, 2017.

Handbook of Pharmaceutical Salts: Properties, and Use, Stahl and Wermuth Eds.), Verlag Helvetica Chimica Acta, 2002.

Hao et al., Current Organic Chemistry: 17, 930-942, 2013.

Hsu et al., 2013

Jarzebinska et al., Angew. Chem. Int. Ed. 55:9591-9595, 2016.

Jarzebinska et al., Angew. Chern. Int. Ed. 55, 9591-9595, 2016.

Jayaraman et al., Maximizing the potency of siRNA lipid nanoparticles for hepatic gene silencing in vivo. Angew. Chem. Int. Ed. 51, 8529-8533, 2012.

Jerome and Lecomte, Advanced Drug Delivery Reviews: 60, 1056, 2008.

Ji et al., MicroRNA expression, survival, and response to interferon in liver cancer. New Engl. J. Med. 361, 1437-1447 (2009).

Jinek et al.

Kabanov et al., FEBS Lett., 259, 327, 1990.

Kaczmarek et al., Angew. Chem. Int. Ed. 55:13808-13812, 2016.

Kaczmarek et al., Angew. Chern. Int. Ed. 55, 13808-13812, 2016.

Kanasty et al., Delivery materials for siRNA therapeutics. Nat. Mater. 12, 967-977, 2013.

Kanasty et al., Nat. Mater. 12, 967-977, 2013.

Kang et al., Tat-conjugated PAMAM dendrimers as delivery agents for antisense and siRNA oligonucleotides. Pharm. Res. 22, 2099-2106 (2005).

Kasinski and Slack, MicroRNAs en route to the clinic: progress in validating and targeting microRNAs for cancer therapy. Nat. Rev. Cancer 11, 849-864 (2011).

Kauffman et al., Nano Lett. 15, 7300-7306, 2015.

Kauffman et al., Nano Lett. 15:7300-7306, 2015.

Khan et al., Ionizable amphiphilic dendrimer-based nanomaterials with alkyl-chain-substituted amines for tunable siRNA delivery to the liver endothelium in vivo. Angew. Chem. Int. Ed. 53, 14397-14401 (2014).

Killops et al., Robust, efficient, and orthogonal synthesis of dendrimers via thiol-ene "click" chemistry. J. Am. Chem. Soc. 130, 5062-5064, 2008.

Kim et al., ACS Macro Letters: 1, 845, 2012.

Kormann et al., Nat. Biotechnol. 29, 154-157, 2011.

Koshkin et al., Tetrahedron, 1998, 54, 3607-3630.

Kota et al., Therapeutic microRNA delivery suppresses tumorigenesis in a murine liver cancer model. Cell 137, 1005-1017 (2009).

Kroschwitz, J. I., Ed., The Concise Encyclopedia Of Polymer Science And Engineering, John Wiley & Sons, 858-859, 1990.

Kumar et al., Bioorg. Med. Chem. Lett., 8, 2219-2222, 1998.

Ladeiro et al., MicroRNA profiling in hepatocellular tumors is associated with clinical features and oncogene/tumor suppressor gene mutations. Hepatology 47, 1955-1963 (2008).

Lee et al., Designing dendrimers for biological applications. Nat. Biotechnol. 23, 1517-1526 (2005).

Lee et al., Journal of Controlled Release: 152, 152, 2011.

Letsinger et al., Proc. Natl. Acad. Sci. USA, 86, 6553, 1989.

Leumann, C J. Bioorg. & Med. Chem. (2002) 10:841-854.

Leung et al., Lipid nanoparticles containing siRNA synthesized by microfluidic mixing exhibit an electron-dense nanostructured core. J. Phys. Chem. C 116, 22104-22104, 2012.

Li et al., Nano Lett. 15, 8099-8107, 2015.

Li et al., Nano Lett. 15:8099-8107, 2015.

Li et al., Sci. Rep. 6:22137, 2016

Ling et al., MicroRNAs and other non-coding RNAs as targets for anticancer drug development. Nat. Rev. Drug Discov. 12, 847-865 (2013).

Love et al., Lipid-like materials for low-dose, in vivo gene silencing. Proc. Natl. Acad. Sci. U.S.A. 107, 1864-1869, 2010.

Lv et al., J. Controlled Release 114, 100-109, 2006.

Lynn and Langer, R. Journal of the American Chemical Society: 122, 10761, 2000.

Ma et al., Facile synthesis of polyester dendrimers from sequential click coupling of asymmetrical monomers. J. Am. Chem. Soc. 131, 14795-14803, 2009.

Mali et al., 2013a, b.

Mali et al., 2013a.

Manoharan et al., Ann. N.Y. Acad. Sci., 660, 306, 1992.

Manoharan et al., Bioorg. Med. Chem. Let., 3, 2765, 1993.

Manoharan et al., Bioorg. Med. Chem. Lett., 4, 1053, 1994.

Manoharan et al., Nucleosides & Nucleotides, 14, 969, 1995.

Manoharan et al., Tetrahedron Lett., 36, 3651, 1995

March's Advanced Organic Chemistry: Reactions, Mechanisms, and Structure, 2007.

Meade et al., Efficient delivery of RNAi prodrugs containing reversible charge-neutralizing phosphotriester backbone modifications. Nat. Biotechnol. 32, 1256-1261 (2014).

Miller et al., Angew. Chem. Int. Ed. 56, 1059-1063, 2017

Mishra et al., Biochim. Biophys. Acta, 1264, 229, 1995.

Murat and Grest, Molecular dynamics study of dendrimer molecules in solvents of varying quality. Macromolecules 29, 1278-1285 (1996).

Nelson et al., C. L. ACS Nano: 7, 8870, 2013.

Nguyen et al., Lin28b is sufficient to drive liver cancer and necessary for its maintenance in murine models. Cancer Cell 26, 248-261, 2014.

Oberhauser et al., Nucl. Acids Res., 20, 533, 1992.

Orum et al., Curr. Opinion Mol. Ther., 2001, 3, 239-243

Pardi et al., J. Controlled Release 217, 345-351, 2015.

Parmar et al., Bioconjugate Chem: 25, 896, 2014.

Patel et al., Nano Lett 17, 5711-5718, 2017.

Percec et al., Self-assembly of Janus dendrimers into uniform dendrimersomes and other complex architectures. Science 328, 1009-1014 (2010).

Petar and. Tomalia, Chem. in Britain, 641-645, August 1994.

Petsch et al., Nat. Biotechnol 30, 1210-1216, 2012.

Philipp et al., Bioconjugate Chem: 20, 2055, 2009.

Pounder and Dove, A. Polym Chem-Uk: 1, 260, 2010.

Ramaswamy et al., Proc. Nat!. Acad. Sci. U.S.A.114, E1941-E1950, 2017.

Richner et al., Cell169, 176, 2017.

Roberts, L.R. Sorafenib in liver cancer—Just the beginning. New Engl. J. Med. 359, 420-422 (2008).

Rossi et al., New hope for a microRNA therapy for liver cancer. Cell 137, 990-992 (2009).

Roush and Slack, The let-7 family of microRNAs. Trends Cell Biol 18, 505-516, 2008.

Sahay et al., Efficiency of siRNA delivery by lipid nanoparticles is limited by endocytic recycling. Nat. Biotechnol. 31, 653-U119, 2013.
Sahin et al., Nat. Rev. Drug Discovery 13, 759-780, 2014.
Saison-Behmoaras et al., EMBO J., 10, 111, 1991.
Sambrook et al., 1989.
Sanghvi, Y. S., Chapter 15, Antisense Research and Applications, Crooke, S. T. and Lebleu, B., Eds., CRC Press, 273-288, 1993.
Schaffert et al., Solid-phase synthesis of sequence-defined T-, i-, and U-shape polymers for pDNA and siRNA delivery. Angew. Chem. Int. Ed. 50, 8986-8989, 2011.
Scholz and Wagner, E. Journal of Controlled Release: 161, 554, 2012.
Schroeder et al., Journal of Controlled Release: 160, 172, 2012.
Scudellari, M. Drug development: Try and try again. Nature 516, S4-S6 (2014).
Semple et al., Rational design of cationic lipids for siRNA delivery. Nat. Biotechnol. 28, 172-176, 2010.
Shachaf et al., MYC inactivation uncovers pluripotent differentiation and tumour dormancy in hepatocellular cancer. Nature 431, 1112-1117 (2004).
Shea et al., Nucl. Acids Res., 18, 3777, 1990.
Siegwart et al., Combinatorial synthesis of chemically diverse core-shell nanoparticles for intracellular delivery. Proc. Natl. Acad. Sci. U.S.A. 108, 12996-13001, 2011.
Silvers et al., Polym Sci Pol Chem; 50, 3517, 2012.
Singh et al., Chem. Commun., 1998, 4, 455-456.
Singh et al., J. Org. Chem., 1998, 63, 10035-10039
Soutschek et al., 2004.
Srivastava et al., J. Am. Chem. Soc., 129 (26) 8362-8379 Jul. 4, 2007.
Stiriba et al., Dendritic polymers in biomedical applications: From potential to clinical use in diagnostics and therapy. Angew. Chem. Int. Ed. 41, 1329-1334 (2002).
Svinarchuk et al., Biochimie, 75, 49, 1993.
Tan et al., Small: 7, 841, 2011.
Taratula et al., Surface-engineered targeted PPI dendrimer for efficient intracellular and intratumoral siRNA delivery. J. Control. Release 140, 284-293 (2009).
Tempelaar et al., Macromolecules, 44, 2084, 2011.
Tian et al., Prog Polym Sci: 37, 237, 2012.
Tousignant et al., Hum. Gene Ther. 11,2493-2513, 2000.
Uchida et al., J. Am. Chem. Soc. 136, 12396-12405, 2014.
Ventura and Jacks, MicroRNAs and cancer: Short RNAs go a long way. Cell 136, 586-591 (2009).
Wadhwa et al., 2004.
Wahlestedt et al., Proc. Natl. Acad. Sci. U.S.A., 2000, 97, 5633-5638.
Whitehead et al., Knocking down barriers: Advances in siRNA delivery. Nat. Rev. Drug Discov. 8, 129-138 (2009).
Whitehead et al., D. NAT REV DRUG DISCOV: 8, 129, 2009.
Whitehead et al., Degradable lipid nanoparticles with predictable in vivo siRNA delivery activity. Nat. Commun. 5, 4277, 2014.
Wu et al., Dendrimers in medicine: Therapeutic concepts and pharmaceutical challenges. Bioconjugate Chem., ASAP (2015).
Wu et al., Efficiency and fidelity in a click-chemistry route to triazole dendrimers by the copper (I)-catalyzed ligation of azides and alkynes. Angew. Chem. Int. Ed. 43, 3928-3932, 2004.
Wu et al., Sci. Trans!. Med. 6, 240-247, 2014.
Yan et al., Biomacromolecules, 18:4307-4315, 2017.
Yin et al., 2014 and Pankowicz et al., 2016.
Yin et al., Nat. Biotechnol. 34:328-333, 2016.
Yin et al., Nat. Biotechnol. 34:328-333, 2016
Zimmermann et al., Nature: 441, 111, 2006.
Zugates et al., Journal of the American Chemical Society: 128, 12726, 2006.

---

What is claimed is:

1. A method for delivering a messenger ribonucleic acid (mRNA) into a cell, the method comprising contacting said cell with a lipid composition encapsulating said mRNA, wherein the lipid composition comprises:

a cationic ionizable lipid at a molar percentage from about 5 to about 30;

a phospholipid at a molar percentage from about 10 to about 45;

a steroid or steroid derivative at a molar percentage from about 15 to about 50; and a polymer-conjugated lipid at a molar percentage from about 1 to about 6, wherein the molar percentage is determined based on the total mols of lipids present in the lipid composition;

thereby delivering said mRNA into said cell, wherein the cationic ionizable lipid is a compound having the structure of Formula (I):

Core-(Repeating Unit)$_n$-Terminating Group          (I), or a pharmaceutically acceptable salt thereof, wherein the compound of Formula (I) or the pharmaceutically acceptable salt thereof is a dendron or dendrimer, wherein:

the core is linked to one or more repeating units, wherein:

the core corresponds to the structure of Formula (IV):

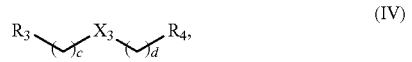          (IV)

wherein, in Formula (IV):

$X_3$ is selected from —NR$_6$—, —O—, substituted or unsubstituted alkylaminodiyl$_{(C \leq 8)}$, substituted or unsubstituted alkoxydiyl$_{(C \leq 8)}$, substituted or unsubstituted arenediyl$_{(C \leq 8)}$, substituted or unsubstituted heteroarenediyl$_{(C \leq 8)}$, and substituted or unsubstituted heterocycloalkanediyl$_{(C \leq 8)}$, wherein R$_6$ is hydrogen, unsubstituted alkyl$_{(C \leq 8)}$, or substituted alkyl$_{(C \leq 8)}$;

R$_3$ and R$_4$ are each independently selected from amino, hydroxy, mercapto, substituted or unsubstituted alkylamino$_{(C \leq 12)}$, and substituted or unsubstituted dialkylamino$_{(C \leq 12)}$; and c and d are each independently 1, 2, 3, 4, 5, or 6;

the repeating unit comprises a degradable diacyl group and optionally a linker; wherein:

the degradable diacyl group has the formula:

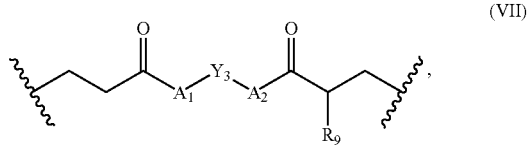          (VII)

wherein, in Formula (VII):

A$_1$ and A$_2$ are each independently —O— or —NR$_a$—, wherein R$_a$ is hydrogen or substituted or unsubstituted alkyl$_{(C \leq 6)}$;

Y$_3$ is selected from substituted or unsubstituted alkanediyl$_{(C \leq 12)}$, substituted or unsubstituted alkenediyl$_{(C \leq 12)}$, substituted or unsubstituted arenediyl$_{(C \leq 12)}$, and a group of the formula:

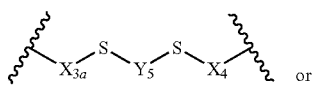 or

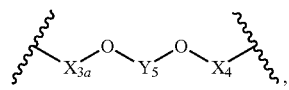, wherein:

X$_{3A}$ and X$_4$ are each independently selected from substituted or unsubstituted alkanediyl$_{(C \leq 12)}$, substituted or unsubstituted alkenediyl$_{(C \leq 12)}$, and substituted or unsubstituted arenediyl$_{(C \leq 12)}$; and Y$_5$ is selected from a covalent bond, substituted or unsubstituted alkanediyl$_{(C \leq 12)}$, substituted or unsubstituted alkenediyl$_{(C\leq12)}$, and substituted or unsubstituted arenediyl$_{(C\leq12)}$; and R$_9$ is substituted or unsubstituted alkyl$_{(C\leq8)}$; and the linker group has the formula:

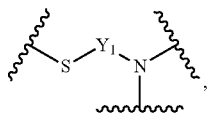

wherein, in Formula (VI):

Y$_1$ is selected from substituted or unsubstituted alkanediyl$_{(C\leq12)}$, substituted or unsubstituted alkenediyl$_{(C\leq12)}$, and substituted or unsubstituted arenediyl$_{(C\leq12)}$; and wherein when the repeating unit comprises a linker group, then the linker group is attached to the degradable diacyl group on both the nitrogen and the sulfur atoms of the linker group, wherein the first group in the repeating unit is the degradable diacyl group, wherein for each linker group, the next group comprises two degradable diacyl groups attached to the nitrogen atom of the linker group; and wherein n is 1, 2, 3, 4, 5, or 6; and the terminating group has the formula:

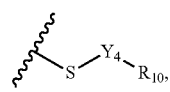

(VIII)

wherein, in Formula (VIII):

Y$_4$ is unsubstituted alkanediyl$_{(C\leq18)}$ or alkanediyl$_{(C\leq18)}$ substituted with one or more substituents independently selected from —OH, —F, —Cl, —Br, —I, —SH, —OCH$_3$, —OCH$_2$CH$_3$, —SCH$_3$, and —OC(O)CH$_3$;

R$_{10}$ is selected from hydrogen, carboxy, hydroxy, aryl$_{(C\leq12)}$, alkylamino$_{(C\leq12)}$, dialkylamino$_{(C\leq12)}$, N-heterocycloalkyl$_{(C\leq12)}$, —C(O)N(R$_{11}$)-alkanediyl$_{(C\leq6)}$-heterocycloalkyl$_{(C\leq12)}$, —C(O)-alkylamino$_{(C\leq12)}$, —C(O)-dialkylamino$_{(C\leq12)}$, and —C(O)—N-heterocyclo-alkyl$_{(C\leq12)}$, wherein:

R$_{11}$ is hydrogen or substituted or unsubstituted alkyl (C≤6); and wherein the final degradable diacyl in the chain of repeating unit(s) is attached to the terminating group.

2. The method of claim 1, wherein, prior to said contacting, said cell exhibits an aberrant expression or activity of the protein encoded by said mRNA.

3. The method of claim 2, wherein said aberrant expression or activity of said protein comprises the expression of a non-functional variant of said protein.

4. The method of claim 3, wherein said aberrant expression or activity of said protein is associated with a genetic disease or disorder.

5. The method of claim 3, wherein said mRNA is expressed in said cell, upon said contacting, to produce a functional variant of said protein.

6. The method of claim 3, wherein the expression of said mRNA in said cell increases the amount of a functional variant of said protein as compared to the amount of said functional variant of said protein generated in absence of said contacting.

7. The method of claim 1, wherein said contacting is in vivo.

8. The method of claim 1, wherein said cell is in a tissue or organ of a subject.

9. The method of claim 8, wherein said tissue or organ is a functionally compromised tissue or organ.

10. The method of claim 1, wherein said contacting comprises administering to said subject said lipid composition assembled with said mRNA.

11. The method of claim 1, further comprising repeating said contacting.

12. The method of claim 1, wherein said contacting comprises contacting a plurality of cells that comprises said cell.

13. The method of claim 12, wherein said mRNA is expressed in at least 40% of said plurality of cells, upon said contacting, to produce a functional variant of the protein encoded by said mRNA.

14. The method of claim 1, wherein the lipid composition comprises said mRNA and said cationic ionizable lipid at a weight ratio from about 1:1 to about 1:100.

15. The method of claim 1, wherein said phospholipid is a zwitterionic phospholipid.

16. The method of claim 1, wherein said phospholipid is 1,2-distearoyl-sn-glycero-3-phosphocholine (DSPC) or 1,2-dioleoyl-sn-glycero-3-phosphoethanolamine (DOPE).

17. The method of claim 1, wherein the lipid composition comprises said polymer-conjugated lipid at a molar percentage from about 1 to about 4, wherein the molar percentage is determined based on the total mols of lipids present in the lipid composition.

18. The method of claim 17, wherein said polymer-conjugated lipid is a polyethylene glycol (PEG)-conjugated lipid.

19. The method of claim 1, wherein said steroid or said steroid derivative comprises a cholesterol moiety.

20. The method of claim 1, wherein, in the compound of Formula (I), or the pharmaceutically acceptable salt thereof, the core corresponds to a structure selected from the group consisting of:

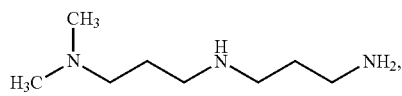

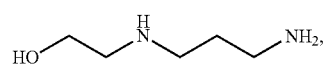

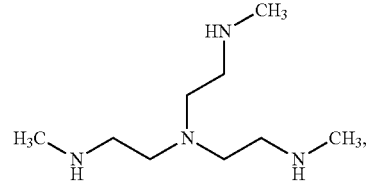

-continued

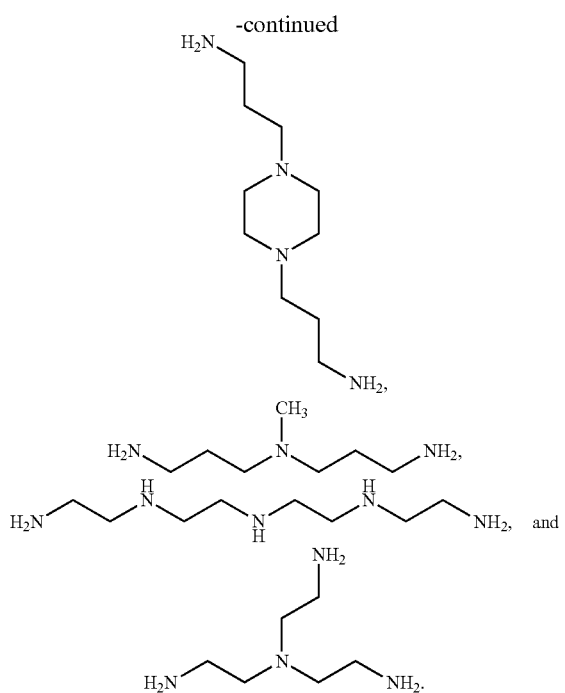

21. The method of claim 1, wherein, in the terminating group of Formula (VIII), $Y_4$ is alkanediyl$_{(C \leq 18)}$; and $R_{10}$ is hydrogen.

22. The method of claim 1, wherein the compound of Formula (I), or the pharmaceutically acceptable salt thereof, is of a generation selected from 0, 1, 2, and 3.

23. The method of claim 1, wherein the lipid composition comprises said cationic ionizable lipid at a molar percentage from about 5 to about 25, wherein the molar percentage is determined based on the total mols of lipids present in the lipid composition.

24. The method of claim 1, wherein the lipid composition comprises said cationic ionizable lipid at a molar percentage from about 5 to about 20, wherein the molar percentage is determined based on the total mols of lipids present in the lipid composition.

25. The method of claim 1, wherein the lipid composition comprises a lipid nanoparticle.

26. The method of claim 1, wherein the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, via a catheter, via a lavage, via continuous infusion, via infusion, via inhalation, via injection, via local delivery, or via localized perfusion.

* * * * *

SEQUENCE LISTING

```
Sequence total quantity: 2
SEQ ID NO: 1           moltype = RNA   length = 711
FEATURE                Location/Qualifiers
misc_feature           1..711
                       note = Synthetic oligoribonucleotide
source                 1..711
                       mol_type = other RNA
                       organism = synthetic construct
SEQUENCE: 1
atggtgagca agggcgagga ggataacatg gccatcatca aggagttcat gcgcttcaag   60
gtgcacatgg agggctccgt gaacggccac gagttcgaga tcgagggcga gggcgagggc  120
cgcccctacg agggcaccca gaccgccaag ctgaaggtga ccaagggtgg cccctgccc   180
ttcgcctggg acatcctgtc ccctcagttc atgtacggct ccaaggccta cgtgaagcac  240
cccgccgaca tccccgacta cttgaagctg tccttccccg agggcttcaa ttgggagcgc  300
gtgatgaact tcgaggacgg cggcgtggtg accgtgaccc aggactcctc cctgcaggac  360
ggcgagttca tctacaaggt gaagctgcgc ggcaccaact tccccctccga cggccccgta  420
atgcagtgtc gtaccatggg ctgggaggcc tccactgagc ggatgtaccc cgaggacggc  480
gccctgaagg gcgagatcaa gcagaggctg aagctgaagg acggcggcca ctacgacgct  540
gaggtcaaga ccacctacaa ggccaagaag cccgtgcagc tgcccggcgc ctacaacgtc  600
gacatcaagt tggacatcct ttcccacaac gaggactaca ccatcgtgga acagtacgaa  660
cgcgccgagg gccgccactc caccggcggc atggacgagc tgtacaagta a           711

SEQ ID NO: 2           moltype = RNA   length = 1260
FEATURE                Location/Qualifiers
misc_feature           1..1260
                       note = Synthetic oligoribonucleotide
source                 1..1260
                       mol_type = other RNA
                       organism = synthetic construct
SEQUENCE: 2
atgtccttta ttccagtggc cgaggactcc gactttccca tccaaaacct gcctatggt    60
```

-continued

```
gttttctcca ctcaaagcaa cccaaagcca cggattggtg tagccatcgg tgaccagatc    120
ttggacctga gtgtcattaa acacctcttt accggacctg ccctttccaa acatcaacat    180
gtcttcgatg agacaactct caataacttc atgggtctgg gtcaagctgc atggaaggag    240
gcaagagcat cettacagaa cttactgtct gccagccaag cccggctcag agatgacaag    300
gagcttcggc agcgtgcatt cacctcccag gcttctgcca caatgcacct tcctgctacc    360
ataggagact acacggactt ctactcttct cggcagcatg ccaccaatgt tggcattatg    420
ttcagaggca aggagaatgc gctgttgcca aattggctcc acttacctgt gggataccat    480
ggccgagctt cctccattgt ggtatctgga accccgattc gaagacccat ggggcagatg    540
agacctgata actcaaagcc tcctgtgtat ggtgcctgca gactcttaga catggagttg    600
gaaatggctt tcttcgtagg ccctgggaac agattcggag agccaatccc catttccaaa    660
gcccatgaac acattttcgg gatggtcctc atgaacgact ggagcgcacg agacatccag    720
caatgggagt acgtcccact tgggccattc ctggggaaaa gctttggaac cacaatctcc    780
ccgtgggtgg tgcctatgga tgccctcatg ccctttgtgg tgccaaaccc aaagcaggac    840
cccaagccct tgccatatct ctgccacagc cagccctaca catttgatat caacctgtct    900
gtctctttga aaggagaagg aatgagccag gcggctacca tctgcaggtc taactttaag    960
cacatgtact ggaccatgct gcagcaactc acacaccact ctgttaatgg atgcaacctg   1020
agacctgggg acctcttggc ttctggaacc atcagtggat cagaccctga aagctttggc   1080
tccatgctgg aactgtcctg gaagggaaca aaggccatcg atgtgggca ggggcagacc   1140
aggaccttcc tgctggacgg cgatgaagtc atcataacag gtcactgcca ggggacggc    1200
taccgtgttg gctttggcca gtgtgctggg aaagtgctgc ctgcccttc accagcctga   1260
```